US012558058B2

(12) United States Patent
Manickam et al.

(10) Patent No.: US 12,558,058 B2
(45) Date of Patent: Feb. 24, 2026

(54) REAL-TIME DOPPLER ULTRASOUND SIGNAL PROCESSING TECHNIQUES FOR FETAL HEART RATE DETECTION WITH SUPERVISORY ERROR CONTROL

(71) Applicant: GE Precision Healthcare LLC, Waukesha, WI (US)

(72) Inventors: Kalaivani Manickam, Solihull (GB); Shrihari Viswanath, Bangalore (IN); Rajendra Naik, Bangalore (IN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/598,159

(22) Filed: Mar. 7, 2024

(65) Prior Publication Data

US 2025/0281153 A1 Sep. 11, 2025

(51) Int. Cl.
*A61B 8/08* (2006.01)
*A61B 8/00* (2006.01)
*A61B 8/02* (2006.01)

(52) U.S. Cl.
CPC .............. *A61B 8/0866* (2013.01); *A61B 8/02* (2013.01); *A61B 8/488* (2013.01); *A61B 8/5207* (2013.01); *A61B 8/5276* (2013.01); *A61B 8/54* (2013.01); *A61B 2503/02* (2013.01)

(58) Field of Classification Search
CPC ..... A61B 5/02411; A61B 8/0866; A61B 8/02; A61B 8/488; A61B 8/5207; A61B 8/5276; A61B 8/54; A61B 2503/02
See application file for complete search history.

(56) References Cited

U.S. PATENT DOCUMENTS

| 11,266,375 | B2 | 3/2022 | Wohlschlager et al. | |
| 2009/0192396 | A1* | 7/2009 | Hayes-Gill | A61B 5/4362 |
| | | | | 600/511 |
| 2014/0276148 | A1* | 9/2014 | Kim | A61B 5/746 |
| | | | | 600/502 |
| 2016/0310062 | A1* | 10/2016 | Larson | A61B 5/0011 |
| 2018/0350468 | A1* | 12/2018 | Friedman | G16H 50/20 |
| 2022/0133213 | A1* | 5/2022 | Pieri | A61B 5/01 |
| | | | | 600/511 |
| 2023/0346234 | A1* | 11/2023 | Sheridan | A61B 5/681 |
| 2024/0389947 | A1* | 11/2024 | Melaet | A61B 5/6823 |

* cited by examiner

*Primary Examiner* — John D Li
(74) *Attorney, Agent, or Firm* — Amin, Turocy & Watson, LLP

(57) ABSTRACT

Techniques for real-time doppler ultrasound signal processing techniques for fetal heart rate (FHR) detection with supervisory error control are provided. In an example, a method comprises receiving, by a system comprising a processor, signal data as the signal data is captured via an ultrasound transducer during a fetal monitoring session using doppler-based ultrasound technology. The method further comprises determining, by the system using a first process, first FHR values for a fetal heart targeted by the ultrasound transducer based on the signal data as the signal data is received, and determining using a second process in parallel with the first process, second FHR values for the fetal heart based on the signal data as the signal data is received. The method further comprises determining, by the system, whether the first FHR values are associated with an error based on differences between the first FHR values and the second FHR values.

17 Claims, 12 Drawing Sheets

Example CTG Tracing with Double Count Errors

500A

2X

2X

501

Fetal Heart Rate (BPM)

240
210
180
150
120
90

Time (minutes)

FIG. 5A

Consecutive signal
data segments

Fixed
Window

Consecutive signal
data segments

Adaptive window
control

Changing
window size

Pattern 1      Pattern 2      Pattern 3      Pattern 4

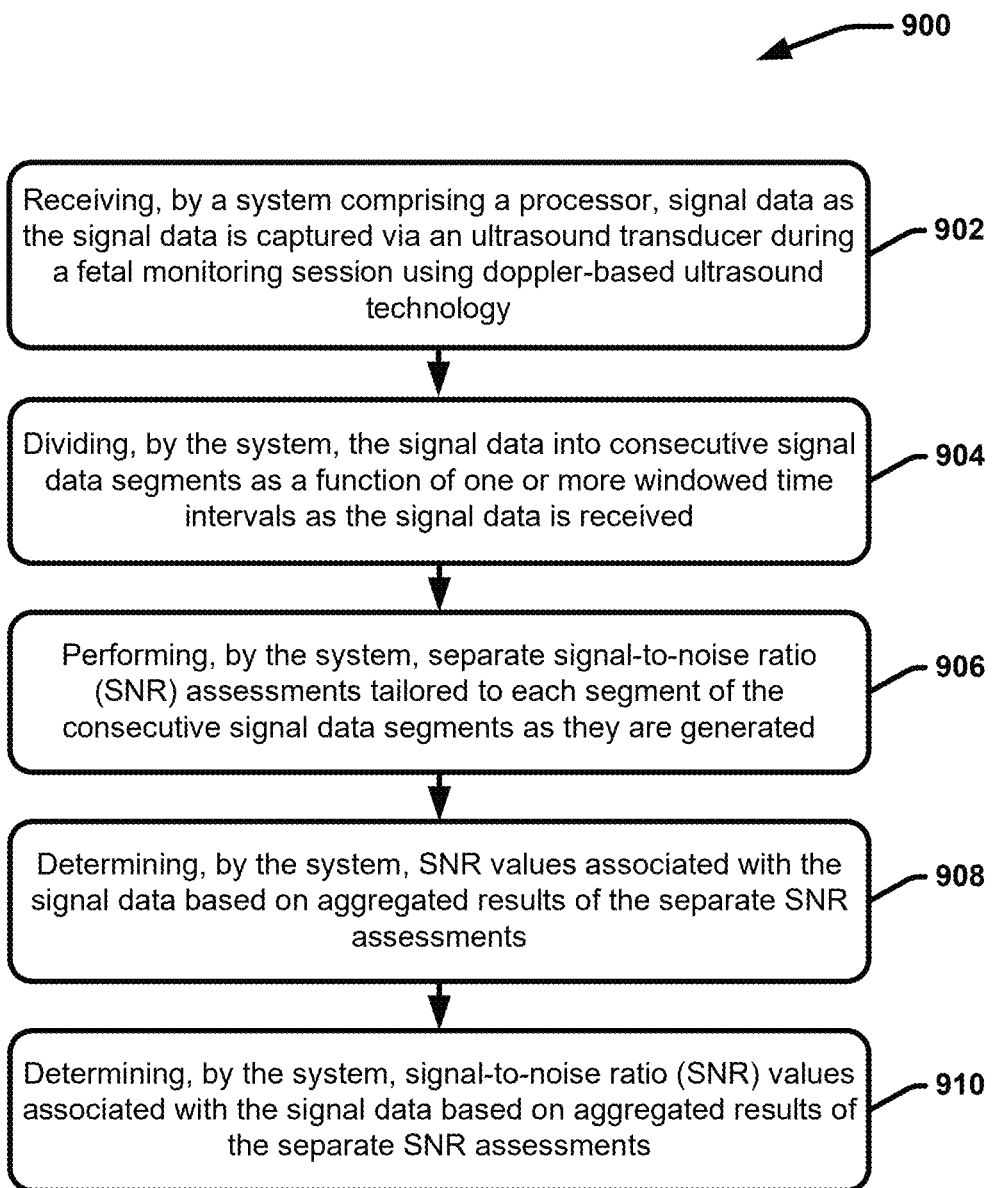

900

Receiving, by a system comprising a processor, signal data as the signal data is captured via an ultrasound transducer during a fetal monitoring session using doppler-based ultrasound technology — 902

Dividing, by the system, the signal data into consecutive signal data segments as a function of one or more windowed time intervals as the signal data is received — 904

Performing, by the system, separate signal-to-noise ratio (SNR) assessments tailored to each segment of the consecutive signal data segments as they are generated — 906

Determining, by the system, SNR values associated with the signal data based on aggregated results of the separate SNR assessments — 908

Determining, by the system, signal-to-noise ratio (SNR) values associated with the signal data based on aggregated results of the separate SNR assessments — 910

FIG. 9

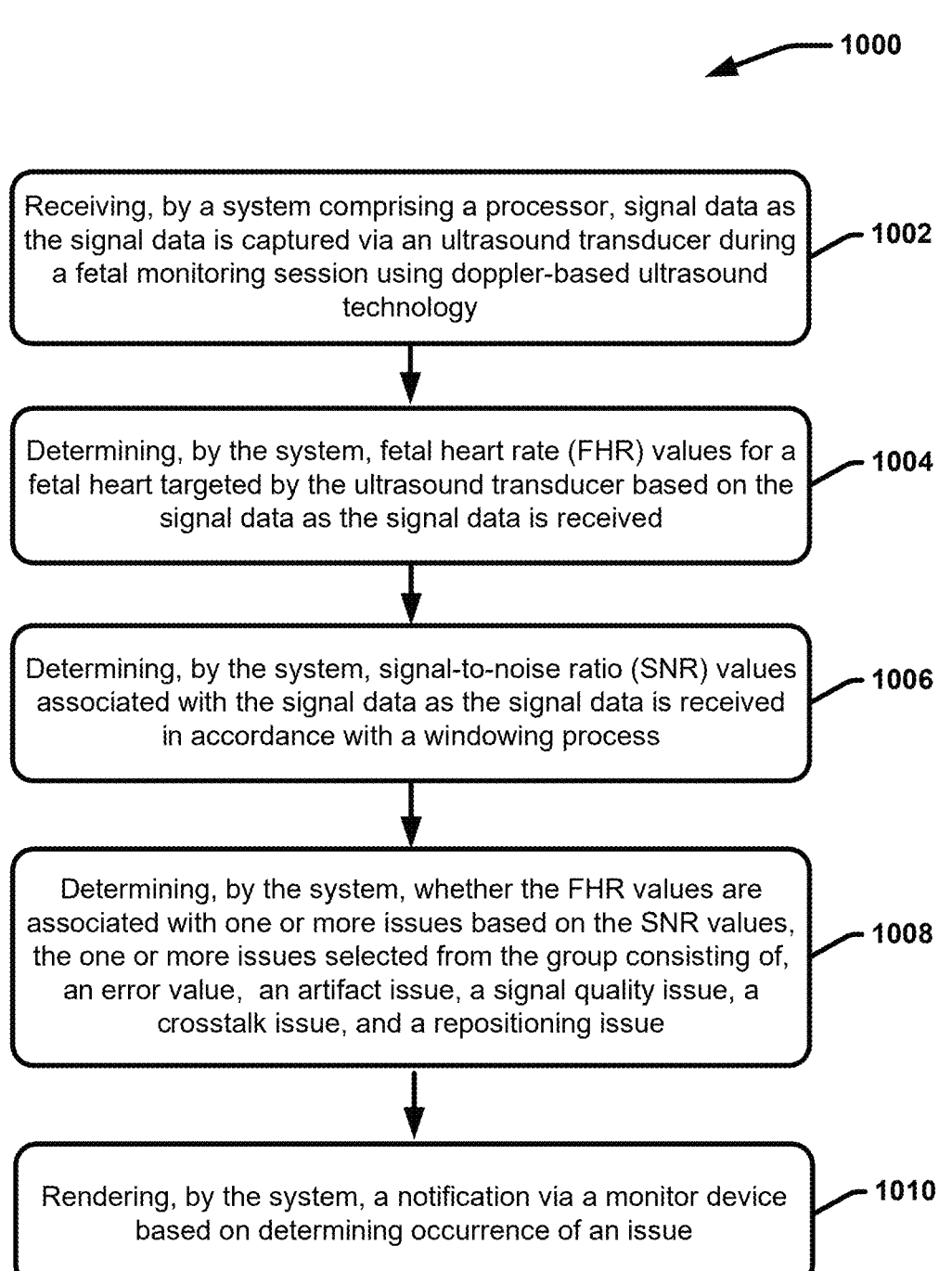

1000

Receiving, by a system comprising a processor, signal data as the signal data is captured via an ultrasound transducer during a fetal monitoring session using doppler-based ultrasound technology — 1002

Determining, by the system, fetal heart rate (FHR) values for a fetal heart targeted by the ultrasound transducer based on the signal data as the signal data is received — 1004

Determining, by the system, signal-to-noise ratio (SNR) values associated with the signal data as the signal data is received in accordance with a windowing process — 1006

Determining, by the system, whether the FHR values are associated with one or more issues based on the SNR values, the one or more issues selected from the group consisting of, an error value, an artifact issue, a signal quality issue, a crosstalk issue, and a repositioning issue — 1008

Rendering, by the system, a notification via a monitor device based on determining occurrence of an issue — 1010

FIG. 10

REAL-TIME DOPPLER ULTRASOUND SIGNAL PROCESSING TECHNIQUES FOR FETAL HEART RATE DETECTION WITH SUPERVISORY ERROR CONTROL

TECHNICAL FIELD

This application relates to doppler ultrasound based fetal heart rate (FHR) monitoring systems, and more particularly to real-time doppler ultrasound signal processing techniques for FHR detection with supervisory error control.

BACKGROUND

Fetal heart rate (FHR) monitoring is a routine procedure during pregnancy check-ups and labor to ensure the baby's health. It helps detect changes in FHR that may indicate distress or other issues, prompting appropriate medical intervention if necessary.

A doppler-based FHR monitoring system is a non-invasive FHR monitoring system that utilizes the Doppler effect to detect changes in as well as the absolute value of the FHR. The Doppler effect is a change in frequency or wavelength of a wave (in this case, ultrasound waves) when the source of the wave and the observer are in relative motion. In the context of FHR monitoring, the Doppler effect is used to detect and measure the fetal heartbeat and fetal movement. A fetal sensor device (FSD) with an ultrasound transducer is placed on the mother's abdomen. The transducer emits sound waves (ultrasound waves) that travel through the mother's tissues and into the uterus. When these ultrasound waves encounter the fetal heart, they are reflected back toward the transducer. Due to the motion of the fetal heart (which beats rhythmically), the frequency of the reflected waves is slightly shifted (Doppler shift) compared to the emitted waves. The Doppler-based monitoring system detects these shifts and calculates the fetal heart rate (FHR) based on the repetitive frequency changes. The results are displayed on a monitor device or printed on a chart, allowing healthcare providers to assess the fetal heart rate and its variability.

Although doppler-based FHR systems serve as a value tool for non-invasively monitoring the well-being of a fetus during pregnancy and labor, there are some challenges and issues associated with the signal processing techniques utilized by these systems for detecting the fetal heart rate. In particular, autocorrelation algorithms are commonly used in doppler-based FHR monitoring to analyze the periodic nature of the doppler signal and extract information about the fetal heart rate. Although autocorrelation algorithms have remained the primary solution for this task, they are not devoid of shortcomings. In this regard, autocorrelation algorithms can be sensitive to the quality of the doppler signal. Poor signal quality, caused by factors such as artifacts, interference, maternal movement, fetal movement, and other factors, can introduce noise and variability in the doppler signal, leading to inaccurate autocorrelation results. This sensitivity may result in false interpretations of the FHR. Autocorrelation algorithms also have limitations in adapting to variations in signal characteristics. Further, some autocorrelation algorithms can be computationally complex, requiring significant processing power and time. In real-time applications, especially in clinical settings, it's important that the signal processing algorithms are efficient and provide accurate results in real-time.

Accordingly, techniques for addressing these limitations associated with autocorrelation algorithms and improving the accuracy and reliability of doppler-based FHR monitoring systems are desired.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that facilitate real-time doppler ultrasound signal processing techniques for FHR detection with supervisory error control.

According to an embodiment, a fetal monitoring system (FMS) is provided that comprises at least one memory that stores computer-executable components, and at least one processor that executes the computer-executable components stored in the at least one memory. The computer-executable components comprise a signal processing component that receives signal data as the signal data is captured via an ultrasound transducer during a fetal monitoring session using doppler-based ultrasound technology. The computer-executable components further comprise a primary fetal heart rate (FHR) estimation component that determines, using a first process, first FHR values for a fetal heart targeted by the ultrasound transducer based on the signal data as the signal data is received. The computer-executable components further comprise a supervisory FHR estimation component that determines, using a second process performed in parallel with first process, second FHR values for the fetal heart based on the signal data as the signal data is received, and an error detection component that determines whether the first FHR values are associated with an error based on differences between the first FHR values and the second FHR values.

In various implementations, the error comprises one or more of the FHR values corresponding to a false value. In some implementations, the error can include at least one of a double-count error or a half-count error.

In some embodiments, based on a determination that one or more of the first FHR values are associated with the error, the error detection component generates error information identifying the error, and wherein the computer-executable components further comprise a rendering component that renders the error information via an electronic output device in association with rendering FHR information indicating the first FHR values. Alternatively, the rendering component can render one or more of the second FHR values corresponding to the one or more first FHR values via the electronic output device as opposed to rendering the one or more of the first FHR values.

In one or more implementations, the second process comprises dividing, via a windowing component of the FMS, the signal data into consecutive signal data segments as a function of a windowed time interval as the signal data is received, and separately evaluating, by the supervisory FHR estimation component, each segment of the consecutive signal data segments as they are generated in association with detecting signal peaks corresponding to heartbeats of the fetal heart. To this end, for each segment, the supervisory FHR estimation component can identify one or more signal peak included in the segment corresponding to a heartbeat of the fetal heart or determine that the segment excludes a signal peak corresponding to the heartbeat. In some implementations, the windowing component employs a fixed duration for the windowed time interval during the fetal monitoring session. In other implementations, the windowing component adapts the duration of the windowed time interval during the fetal monitoring session based on one or more parameters determined using the first process. With these embodiments, for each segment, the supervisory FHR estimation component can identify only a single peak included in the segment corresponding to a heartbeat of the fetal heart or determine that the segment excludes a signal peak corresponding to the heartbeat.

In another embodiment, a fetal monitoring system (FMS) is provided that comprises at least one memory that stores computer-executable components, and at least one processor that executes the computer-executable components stored in the at least one memory. The computer-executable components comprise a signal processing component that receives signal data as the signal data is captured via an ultrasound transducer during a fetal monitoring session using doppler-based ultrasound technology. The computer-executable components further comprise a windowing component that divides the signal data into consecutive signal data segments as a function of one or more windowed time intervals as the signal data is received. The computer-executable components further comprise a signal-to-noise ratio (SNR) assessment component that performs separate signal-to-noise ratio (SNR) assessments tailored to each segment of the consecutive signal data segments as they are generated, determines SNR values associated with the signal data based on aggregated results of the separate SNR assessments, and generates signal quality information indicating a measure of quality of the signal data as the signal data is received based on the SNR values.

In some implementations, the computer-executable components further comprise a rendering component that renders the signal quality information via an electronic output device as the signal quality information is generated.

The computer-executable components can further comprise an artifact assessment component that determines artifact information regarding artifacts reflected in the signal data based on the SNR values. In some embodiments, the artifact assessment component can identify artifact signal peaks associated with the consecutive signal data segments corresponding to artifacts and the SNR assessment component can exclude the artifact signal peaks in association with determining the SNR values.

The computer-executable components can further comprise a crosstalk assessment component that identifies a crosstalk condition associated with the signal data as the signal data is received based on a pattern reflected in the SNR values corresponding to the crosstalk condition, and generates a crosstalk notification identifying the crosstalk condition. The crosstalk assessment component can also facilitate detecting and correcting errors in FHR values determined based on portions of the signal data associated with the crosstalk condition.

The computer-executable components can further comprise an adaptive averaging component that regulates an amount of averaging of the FHR values during the fetal monitoring session based on the SNR values.

The computer-executable components can further comprise a repositioning assessment component that monitors the SNR values during the fetal monitoring session and generates a repositioning indication recommending repositioning of the ultrasound transducer based on detecting a decline in the SNR values in association with the monitoring.

In some embodiments, elements described in connection with the disclosed FMS can be embodied in different forms such as a computer-implemented method, a computer program product, or another form.

DESCRIPTION OF THE DRAWINGS

FIG. 5A presents an example cardiotocography tracing comprising double-count errors, in accordance with one or more embodiments of the disclosed subject matter.

FIG. 9 illustrates a block diagram of another example, non-limiting computer implemented method that facilitates real-time doppler ultrasound signal processing for fetal heartbeat detection with supervisory error control, in accordance with one or more embodiments of the disclosed subject matter.

FIG. 10 illustrates a block diagram of another example, non-limiting computer implemented method that facilitates real-time doppler ultrasound signal processing for fetal heartbeat detection with supervisory error control, in accordance with one or more embodiments of the disclosed subject matter.

DETAILED DESCRIPTION

Figure 1:
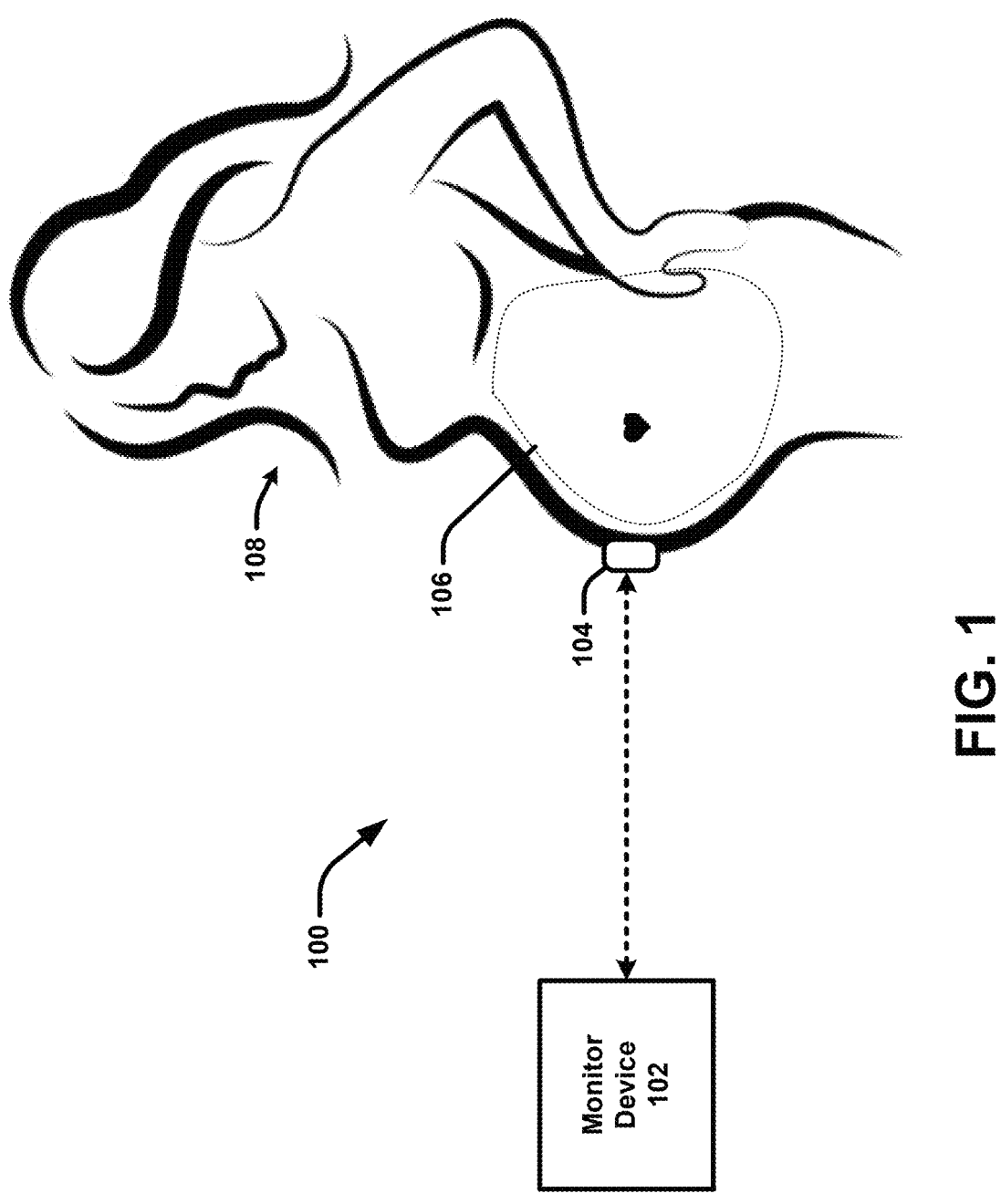
FIG. 1 presents an example fetal monitoring system (FMS) in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The subject disclosure provides systems, computer-implemented methods, apparatus and/or computer program products that facilitate real-time doppler ultrasound signal processing techniques for FHR detection with supervisory error control.

As described in the Background section autocorrelation algorithms typically used in doppler-based FHR monitoring to detect the FHR can be sensitive to noise and variability in the doppler signal and limited in their ability to adapt to variations in signal characteristics due to fetal movement and other physiological factors. These characteristics can result in false interpretations of the FHR. One example of such false interpretations of the FHR that has remained a longstanding issue with doppler-based FHR monitoring systems includes the half-count (HC) and double-count (DC) interpretations. A half-count refers to the observation of only half of the expected number of fetal heartbeats in a given time period, resulting in a false low FHR value. A double count refers to the observation of an apparent duplication or doubling of the number of fetal heartbeats in a given time period, resulting in a false high FHR value. With current FHR monitoring systems, theses false, abnormally high and abnormally low FHR values are not detected by the signal-processing functionality employed by the FHR monitoring system and must be manually detected in association with reviewing the rendered FHR data via the monitor and/or the printed CTG tracing.

More particularly, FHR ranges supported by most doppler-based FHR monitoring systems fall in the range from about 50 beats per minute (BPM) to about 210 BPM. When the FHR drops to low values within this range (e.g., less than about 120 BPM), the autocorrelation algorithm can falsely interpret both the movements of the heart (diastole and systole) as beats leading to the FHR trace doubling in value (i.e., double counting). When the FHR increases to high values within this range (e.g., greater than about 180 BPM), the movements become close enough that a couple of the beats get clumped together by the autocorrelation algorithm and interpreted as a single beat thus the FHR value drops to half the value (half counting). Due to the large range of values that need to be supported by the FMS, some precision at the extreme ends of the range is lost, especially with outliers in the signal morphology.

In one or more embodiments, the disclosed subject matter provides techniques for automatically (e.g., as opposed to manually) detecting errors in FHR values generated by an autocorrelation signal processing algorithm in real-time using a parallel supervisory signal processing process. These errors can include HC/DC errors as well as other false or spurious FHR values. As described in greater detail infra, in various embodiments, the parallel supervisory signal processing process can facilitate automatically detecting such errors using a unique windowing based peak detection approach tailored to perform more reliably in extreme ends of the FHR range supported by the FMS. In some implementations, the FMS can alert the clinician (e.g., via error detection alert information displayed and/or rendered via the monitor device of the FMS) regarding any detected errors in real-time and/or optionally automatically correct the corresponding FHR calculation in real-time, thereby minimizing false interpretations of the doppler-signal in real-time. In some implementations, the FMS can also control generation of alarms (e.g., false alarms) by the FMS or an external system (e.g., an alarm system employed by a neonatal intensive care unit (NICU) involving monitoring multiple patients collectively) regarding occurrences of extremely low/high FHRs in scenarios in which the extremely low/high FHRs are attributed to detected HC/DC errors to reduce alarm fatigue, assigning lower priorities to the same and optionally dismissing them once the HC/DC instance has passed.

In addition, the disclosed techniques provide a novel SNR calculation methodology that uses the output of the windowing based peak detection approach to identify valid peaks and selectively interpret the signals of interest, thus excluding artifacts while calculating the SNR of the doppler signal in real-time. In some implementations, the disclosed techniques can also employ one or more accelerometers on the FSD and couple information from the accelerometer(s) to account for peaks due to artifacts resulting from maternal movement and their selective elimination to improve the accuracy of the SNR calculation and the parallel supervisory process.

In various embodiments, the FMS can employ the SNR values calculated in real-time in accordance with the disclosed techniques to further provide various performance optimization features of the FMS. In some implementations, the FMS can use of the SNR values to determine the accuracy of the parallel supervisory process, with the option of preventing or minimizing influence of the output of the parallel supervisory process on the rendered FHR values at relatively low SNRs (e.g., relative to one or more threshold values). The FMS can also generate a signal quality indicator (e.g., a percentage, a score, or another metric indicative of the quality of the doppler signal in real-time) along with an early repositioning notification recommending repositioning of the FSD as positioned on the mother (e.g., to avoid loss of the FHR) as determined based on the SNR calculation. The repositioning notification can be implemented by observing a steady decline in the SNR values which would indicate the fetus's movement away from the beam of the ultrasound transducer of the FSD. The FMS can also employ the SNR values to identify instances of crosstalk (e.g., in scenarios in which two or more FSDs are used to simultaneously monitor a corresponding number of fetuses of the same mother) and interference by looking for specific behavior in SNR of the signal as the harmonics would be repetitive and at higher frequencies than expected. To this end, the FMS can identify and deal with crosstalk issues accordingly (e.g., via generating and rendering preventive warnings and/or automatically correcting errors in FHR calculations and other fetal parameter calculations such as fetal movement attributed to the crosstalk and/or interference).

The FMS can also employ the SNR values in association with selectively averaging (or not) of the rendered FHR output, using SNR as the process variable. Averaging of the FHR output refers to averaging two or more consecutive FHR values measured over time. In various embodiments, the FMS can perform averaging of the FHR output, and selectively decrease (e.g., to a degree of no averaging) and increase the amount of averaging of the rendered FHR output based on the SNR of the doppler signal. For example, if the SNR of the doppler signal is high (e.g., relative to a defined threshold or range), then the FMS can measure and render the FHR based on real-time beat to beat time differences, and not perform any averaging of consecutive FHR values. On the other hand, if the SNR is low (e.g., relative to one or more defined thresholds or threshold ranges), then the FMS can average two or more consecutive FHR values.

In some implementations, the FMS can tailor the amount of the averaging with respect to the number of consecutive FHR values averaged, based on the SNR such that as the SNR decreases, the number of consecutive FHR values averaged increases. By removing the averaging when the SNR of the signal is high (e.g., relative to one or more thresholds), the FMS can generate and/or facilitate a more accurate, real-time interpretation of the FHR, resulting in better clinical outcomes. Further, differences between the SNR values produced using the disclosed novel SNR calculation techniques and thresholding techniques can help generate metrics related to the amount of artifact in the signal that can be used to warn the clinician or actively compensate for the same.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 presents an example FMS 100 in accordance with one or more embodiments of the disclosed subject matter. The FSM 100 includes a monitor device 102 and a fetal sensor device (FSD) 104. The FSD 104 corresponds to a small, non-invasive medical device comprising an ultrasound transducer configured to measure signals representative of one or more fetal parameters of a fetus using doppler-based ultrasound technology in association with placement of the FSD 104 on the external body of the mother 108. The one more fetal parameters measured by the FSD 104 can include, but are not limited to, FHR, fetal movement, and fetal depth. For example, the FSD 104 is typically placed on the external surface of the abdomen to allow the mother 108 to comfortably lay on her back during the monitoring session. However, in some implementations, the FSD 104 may be positioned on the side body and/or the mother's back. The FSD 104 may be held in place using straps or another suitable mechanism once the FSD has been placed in an optimal position on the mother's body in which it is accurately picking up the heart rate of the fetus in focus.

Over the course of a fetal monitoring session, the FSD 104 can be configured to send raw and/or processed signal data representative of the one or more fetal parameters to the monitor device 102 for additional processing and/or rendering via one or more suitable output devices of the monitor device 102 (e.g., a display, a speaker, etc.). Additionally, or alternatively, some or all of the signal processing can be performed by the monitor device 102. For example, the FSD 104 can be configured to send raw doppler shifted signals to the monitor device 102 for signal processing and/or send partially processed signals (e.g., demodulated signals, digitized signals, etc.) to the monitor device 102 which in turn can process the raw or partially processed signals to calculate the FHR, fetal movement, fetal position/depth, and so on. With these embodiments, any information determined by the monitor device 102 based on processing of the raw or partially processed signals (and/or other information, such as control commands, configuration commands, context information, etc.) may be communicated back to the FSD 104 for usage thereof.

The monitor device 102 and the FSD 104 can be communicatively coupled via any suitable wired or wireless communication technology. For example, in some embodiments, the FSD 104 includes or corresponds to a wireless FSD powered via an onboard power source, such as one or more batteries. In some implementations of these embodiments, the monitor device 102 and the FSD 104 can respectively be configured to communicate information between one another using any suitable wireless communication technology, such as but not limited to: Bluetooth™, Wireless Fidelity (Wi-Fi), near field communication (NFC), Zigbee™, Z-Wave™ infrared (IR), ultra-wideband (UWB), body area network (BAN) communication technologies, medical body area network (MBAN) communication technologies, cellular, and various other existing and foreseen wireless communication technologies. In some embodiments, the wireless communication technology can include a wireless communication technology tailored for performance under water to enable usage of the FSD 104 for monitoring FHR data in water birth scenarios. Additionally, or alternatively, the FSD 104 and the monitor device 102 may be communicatively coupled to one another via one or more wired communication technologies. In some implementations of these embodiments, the FSD 104 can receive power from the monitor device 102 via one or wired power connections and/or another external power source via one or more wired power connections.

In the example embodiment illustrated in FIG. 1, a single FSD 104 is being used in the context of a single fetus (represented by the heart symbol depicted within the womb 106 of the mother 108). However, the FMS 100 can be tailored to different usage scenarios involving simultaneously monitoring different numbers of fetuses and thus different numbers of FSDs 104, one or for each fetus. For example, the FMS 100 can be tailored in association with using a single FSD 104 to monitor a single fetus, two FSDs 104 to respectively monitor two fetuses (i.e., twins), three FSDs 104 to respectively monitor three fetuses (i.e., triplets), four FSDs 104 to respectively monitor four fetuses (i.e., quadruplets), and so on.

The FSD 104 can include suitable hardware and/or software that enables the operations described with respect to the FSD 104 as disclosed herein. For example, in some embodiments, FSD 104 can include an onboard power source (e.g., one or more batteries or another suitable power source), a memory and a processor that enable onboard signal processing functionality and other computer-executable functions described herein, wireless or wired communication hardware and software that enable wired and/or wired communication between the FSD 104 and the monitor device 102, one or more sensors that provide for sensing various parameters associated with the FSD, the mother 108 and/or the fetus (e.g., an accelerometer and/or other types of motion sensors, proximity sensors, contact sensors, temperature sensors, etc.), and other suitable hardware and/or software described with reference to FIG. 2.

Figure 2:
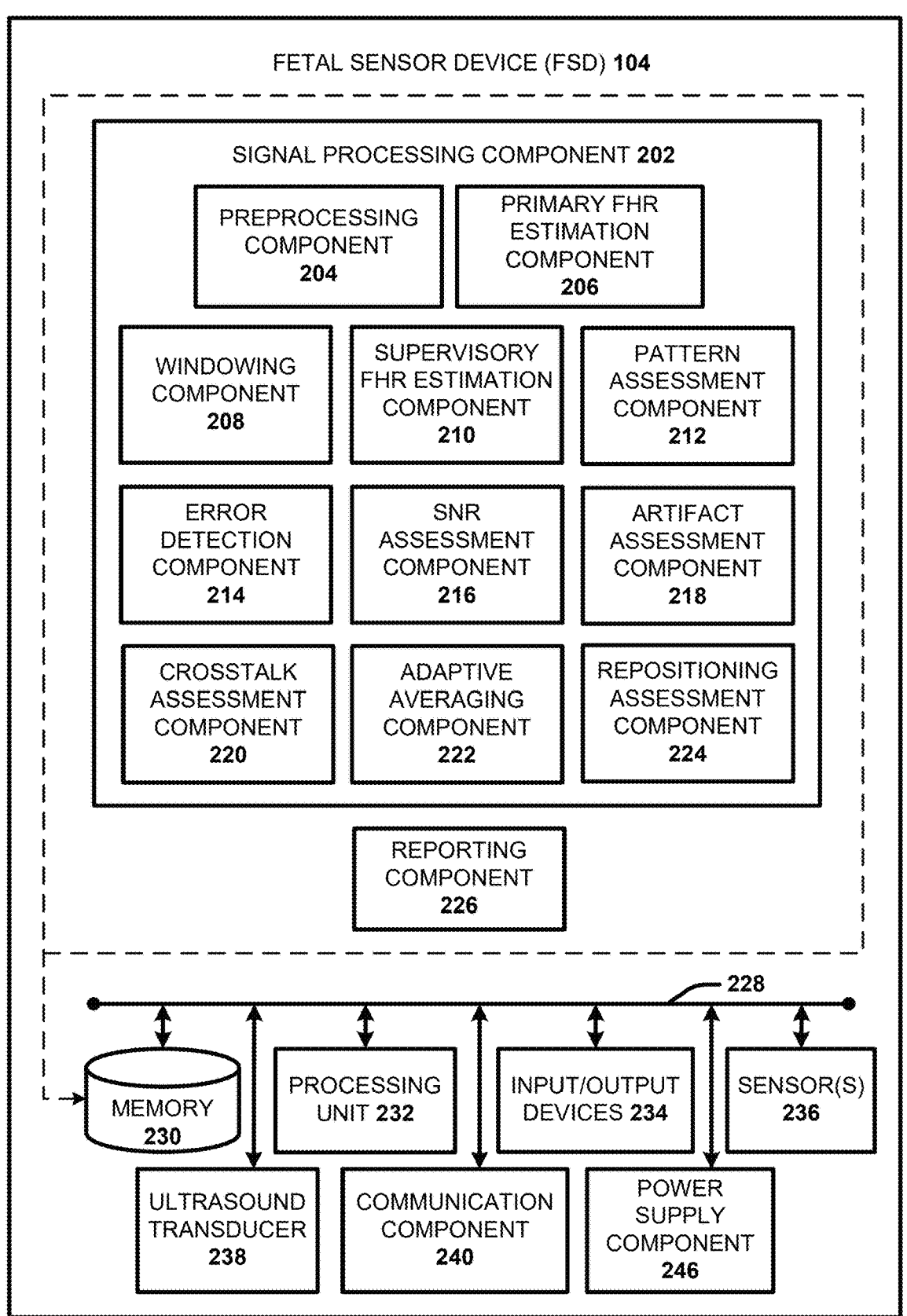
FIG. 2 illustrates a block diagram of an example, non-limiting fetal sensor device (FSD) of a FMS in accordance with one or more embodiments of the disclosed subject matter.

FIG. 2 illustrates a block diagram of an example, non-limiting FSD 104 in accordance with one or more embodiments of the disclosed subject matter. With reference to FIGS. 1 and 2, as mentioned with reference to FIG. 1, the FSD 104 can include an ultrasound transducer 238 configured to measure signals representative of one or more fetal parameters (e.g., FHR, fetal movement, fetal depth, and other potential parameters) of a fetus using doppler-based ultrasound technology in association with positioning of the FSD 104 on an external body of the mother 108. The ultrasound transducer 238 comprises a transmitter/receiver element, typically comprising one or more crystals and/or a piezoelectric element, that generates ultrasound waves when an electric current is applied to it (e.g., via the power supply component 246 or another power source such as an external, wired power source in some embodiments). The transmitter/receiver element is integrated within a head portion of the FSD housing that is placed in direct contact with the mother's skin. The transmitter/receiver element of the ultrasound transducer 238 transmits an ultrasound carrier signal of given carrier frequency and amplitude in a pulsed manner over a transmission (Tx) period. The transmitter/receiver element of the ultrasound transducer 238 also receives any reflected ultrasound waves that may be reflected by tissues of the body, including the targeted fetal heart, over a receive (Rx) period following the Tx period. Over the course of operation, the ultrasound transducer 238 operates by continuously alternating between Tx and Rx periods to track the FHR over the duration of a monitoring session. Due to the motion of the fetal heart (which beats rhythmically), the frequency of the reflected ultrasound waves is slightly shifted (doppler shifted) compared to the emitted waves. This shift is proportional to the intensity of the movement of the fetal heart in association with generating a heartbeat. These shifts can be detected and used to calculate the fetal heart rate (FHR) and fetal movement (e.g., via signal processing component 202 and/or via master signal processing component 306 as deployed on the monitor device 102) based on the repetition rate of the frequency changes using one or more signal processing algorithms. As described in greater detail below, in accordance with the various embodiments, the one more signal processing algorithms can include a primary FHR estimation algorithm and a supervisory FHR estimation algorithm that facilitates detecting and optionally correcting errors (e.g., false values, HC/DC errors, etc.) associated with FHR values generated using the primary FHR estimation algorithm.

In some implementations, the FSD 104 can include one or more input/output devices 234 to facilitate manually configuring the device and displaying data (e.g., operating settings, fetal parameters, battery level, etc.) to users in association with usage of the FMS 100. Suitable examples of the input/output devices 234 are described with reference to FIG. 11 (e.g., input devices 1128 and output device 1136). The FSD 104 can also include a communication component 224 that includes or corresponds to hardware and/or software that enables wired and/or wireless communication between the FSD 104 and the monitor device 102, and optionally enables wired and/or wireless communication between the FSD 104 and other FSDs activated for the monitoring session in a peer-to-peer fashion (e.g., as applied to monitoring two or more fetuses simultaneously). In some embodiments (e.g., in which the FSD 104 corresponds to a wireless device), the FSD 104 can also include a power supply component 246 that corresponds to any suitable onboard power source (e.g., one or more batteries, one or more rechargeable batteries, or another suitable power source).

The FSD 104 can also include one or more sensors 236. In various embodiments, the one or more sensors 236 can include or correspond to a motion sensor, such as an accelerometer and/or another type of motion sensor. As described in greater detail infra, in some implementations of these embodiments, motion data captured via the motion sensor over the course of a monitoring session can be used (e.g., via the artifact assessment component 218) to facilitate detecting artifacts in the doppler signal received by the ultrasound transducer 238 attributed to movement or motion of the mother 108.

The FSD 104 can further include at least one memory 230 that stores machine-executable or computer-executable components or instructions embodied within one or more machines (e.g., embodied in one or more computer-readable storage media associated with one or more machines), and a processing unit 232 that executes the computer-executable components stored in the at least one memory 230. These computer-executable components can include (but are not limited to) signal processing component 202 and reporting component 226. The signal processing component 202 can perform various signal processing functions related to extracting and determining parameters from the raw, doppler-shifted signal data received by the ultrasound transducer 238, including FHR values and other fetal parameters (e.g., fetal movement, fetal depth, etc.), calculating the SNR of the signal data, detecting artifacts, and various other signal processing functions. These signal processing functions are discussed in greater detail below. The reporting component 226 can control reporting (e.g., sending, transmitting, or otherwise communicating) information received by the ultrasound transducer 238 (e.g., raw signal data), the one or more sensors 236 (e.g., raw motion data) and/or generated by the signal processing component 202 to the monitor device 102 in accordance with a defined reporting protocol. Examples of said and memory and processor as well as other suitable computer or computing-based elements, can be found with reference to FIG. 11 (e.g., processing unit 1104 and system memory 1106 respectively), and can be used in connection with implementing one or more of the systems or components shown and described in connection with FIGS. 1 and 2, or other figures disclosed herein.

The FSD 104 can further include a system bus 228 that couples the memory 230, the processing unit 232, the input/output devices 234, the one or more sensors 236, the ultrasound transducer 238, the communication component 240 and the power supply component 246 to one another.

Figure 3:
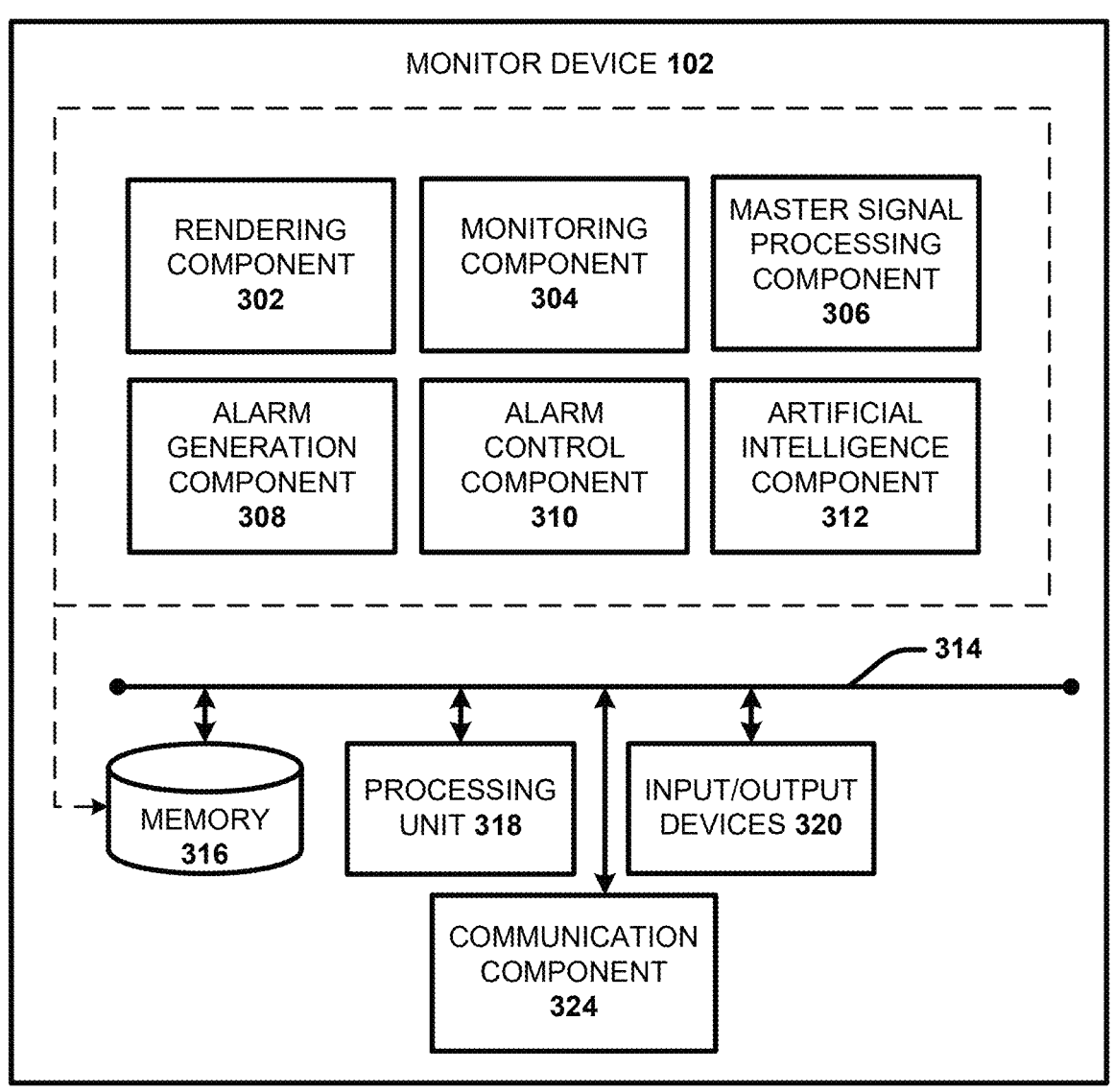
FIG. 3 illustrates a block diagram of an example, non-limiting fetal monitor device of a FMS in accordance with one or more embodiments of the disclosed subject matter.

FIG. 3 illustrates a block diagram of an example, non-limiting monitor device 102 in accordance with one or more embodiments of the disclosed subject matter. With reference to FIGS. 1-3, as mentioned with reference to FIG. 1, the monitor device 102 can be configured to receive raw information captured by the one or more FSDs 104 (e.g., raw doppler ultrasound signal data, raw motion sensor data, etc.) and/or processed information determined by the one or more FSDs 104 and/or the monitor device 102 (e.g., via signal processing component 202 and/or master signal processing component 306, respectively) based on real-time processing of the raw information captured by the one or more FSDs 104 over the course of the monitoring session (e.g., processed doppler ultrasound signal data, FHR data, other fetal parameters data, detected error data, signal quality data, signal artifact data, repositioning indication data, etc.). The monitor device 102 can further be configured to generate and/or render output data (e.g., via rendering component 302) representing the raw and/or processed information in real-time over the course of the fetal monitoring session via one or more suitable electronic output devices. To facilitate this end, monitor device 102 can include communication component 324 and one or more input/output devices 320. The communication component 324 can include or corresponds to hardware and/or software that enables wired and/or wireless communication between the monitor device 102 and the FSDs 104 using any suitable wired or wireless communication technology. In some implementations, the communication component 324 can also enable wired and/or wireless communication between the monitor device 102 and other external devices or systems using any suitable wired or wireless communication technology.

The one or more input/output devices 320 can include one or more suitable electronic input and/or output device that facilitate receiving user input and/or rendering output data (e.g., via rendering 302) to users in association with usage of FMS 100. In various embodiments, the input/output devices 302 can include a display monitor and/or a speaker via which the monitor device 102 renders (e.g., via rendering component 302) information (e.g., visual and/or audible information) over the course of a fetal monitoring session regarding one or more fetal parameters of the corresponding fetuses being monitored in real-time. For example, the monitor device 102 can be configured to render a CTG tracing via a display monitor that provides a graphical representation of the FHR values tracked in real-time over the duration of the fetal monitoring session. The monitor device 102 can also be configured to render audible data that represents the same (e.g., via one or more speakers). The monitor device 102 can also be configured to render the current FHR value (which may be an averaged value) via the display monitor (e.g., as a graphical, digital value) as updated in real-time over the course of the monitoring session. In another example, the input/output devices 320 can include a printer via which the monitor device prints the CTG tracing data on a strip of paper in real-time over the course of the monitoring session. With these embodiments, other information determined/generated by the FSD 104 and/or the monitor device (e.g., information regarding detected errors, artifacts, signal quality, etc.) can also be printed on the strip of paper in real-time over the course of the monitoring session. The monitor device 102 can also be configured to render visual and/or audible output data regarding other fetal parameters determined and tracked over the course of the monitoring session (e.g., fetal depth, fetal movement, etc.). The information rendered via the monitor device 102 is not limited to data representing the monitored fetal parameters (e.g., FHR, fetal position/depth, and/or fetal movement). In this regard, any information associated with the FSDs 104 (e.g., received by, captured by, determined by, stored by, etc.) and/or the monitor device 102 (e.g., received by, captured by, determined by, stored by, etc.) may be rendered via the monitor device 102 using one or more suitable electronic output devices (e.g., a graphical display, a speaker, a printer, or another suitable output device). For instance, additional examples of information that may be rendered via the monitor device 102 can include, but is not limited to, error information regarding errors in FHR values (e.g., false values, HC/DC error values, etc.), alarms, notifications, and various other types of output data discussed herein.

Monitor device 102 can also include at least one memory 316 that stores machine-executable or computer-executable components or instructions embodied within one or more machines (e.g., embodied in one or more computer-readable storage media associated with one or more machines), and a processing unit 318 that executes the computer-executable components stored in the at least one memory 316. These computer-executable components can include (but are not limited to) rendering component 302, monitoring component 304, master signal processing component 306, alarm generation component 308, alarm control component 310 and artificial intelligence component 312. Examples of said and memory and processor as well as other suitable computer or computing-based elements, can be found with reference to FIG. 11 (e.g., processing unit 1104 and system memory 1106 respectively), and can be used in connection with implementing one or more of the systems or components shown and described in connection with FIGS. 1-3, or other figures disclosed herein.

The rendering component 302 can control rendering of output data by the monitor device 102, including controlling timing of rendering (e.g., in real-time and/or in accordance with another defined rendering protocol), format of rendering, and so on. In this regard, the rendering component 302 can generate, format and render the output data in accordance with a defined rendering protocol for the respective types of the output data and the FMS 100. In some embodiments, the monitoring component 304 can be configured to receive and monitor all data provided by the one or more FSDs 104 over the course of a monitoring session in association with detecting characteristics of the data prompting a response by the monitor device 102 in accordance with one or more defined protocols, whether it be additional processing (e.g., via the master signal processing component 306), rendering, generating an alarm or notification (e.g., via alarm generation component 308), controlling alarm generation via the monitor device or an external device/system (e.g., via alarm control component 310), and so on. For example, in some implementations, the monitoring component 304 be configured to detect issues or potential issues associated with a monitored fetus based on values of the one or more parameters being indicative of an issue or potential issue. The monitor device 102 can further generate and render suitable notifications or alarms regarding the detected issues or potential issues (e.g., via alarm generation component 308).

In some embodiments, the master signal processing component 306 can perform the same or similar functions as signal processing component 202. For example, the one or more signal processing functions described with respect to signal processing component 202 (and the corresponding components thereof) may be executed by the monitor device 102 (e.g., via master signal processing component 306) as opposed to and/or in addition to the FSD 104. Repetitive description of these signal processing functions as executed by the signal processing component 202 (at the FSD 104) and/or the master signal processing component 304 (at the monitor device 102) is omitted for sake of brevity, unless context warrants particular distinction between the respective components as described herein.

In one or more embodiments, the signal processing functionality provided by the signal processing component 202 (and/or the master signal processing component 306) can facilitate detecting and responding to potential errors in FHR parameter values (e.g., false values, HC/DC errors, etc.) determined based on the doppler-shifted signal data (also referred to herein simply as "signal data") received by the ultrasound transducer 238 over the course of a monitoring session in real-time using a first process (e.g., a first signal processing process). To facilitate this end, the signal processing component 202 (and/or the master signal processing component 306) can perform one or more second process (e.g., one or more second signal processing process) in parallel with the first process tailored to more accurately calculate the FHR relative to the first process when the FHR is near the extreme ends (e.g., less than about 120 BPM and greater than about 180 BPM) of the discernable FHR range detectable by the FMS 100 (e.g., between about 30 BPM and about 210 BPM). As described in greater detail below, the one or more second processes can include or correspond to one or more windowing signal processing functions that can be used to determine the FHR values in addition to (and in some implementations in alternative to) the first process. The one or more second processes can also include a peak enhancement process, one or more pattern classification and detection processes and/or one or more SNR calculation processes.

Figure 4:
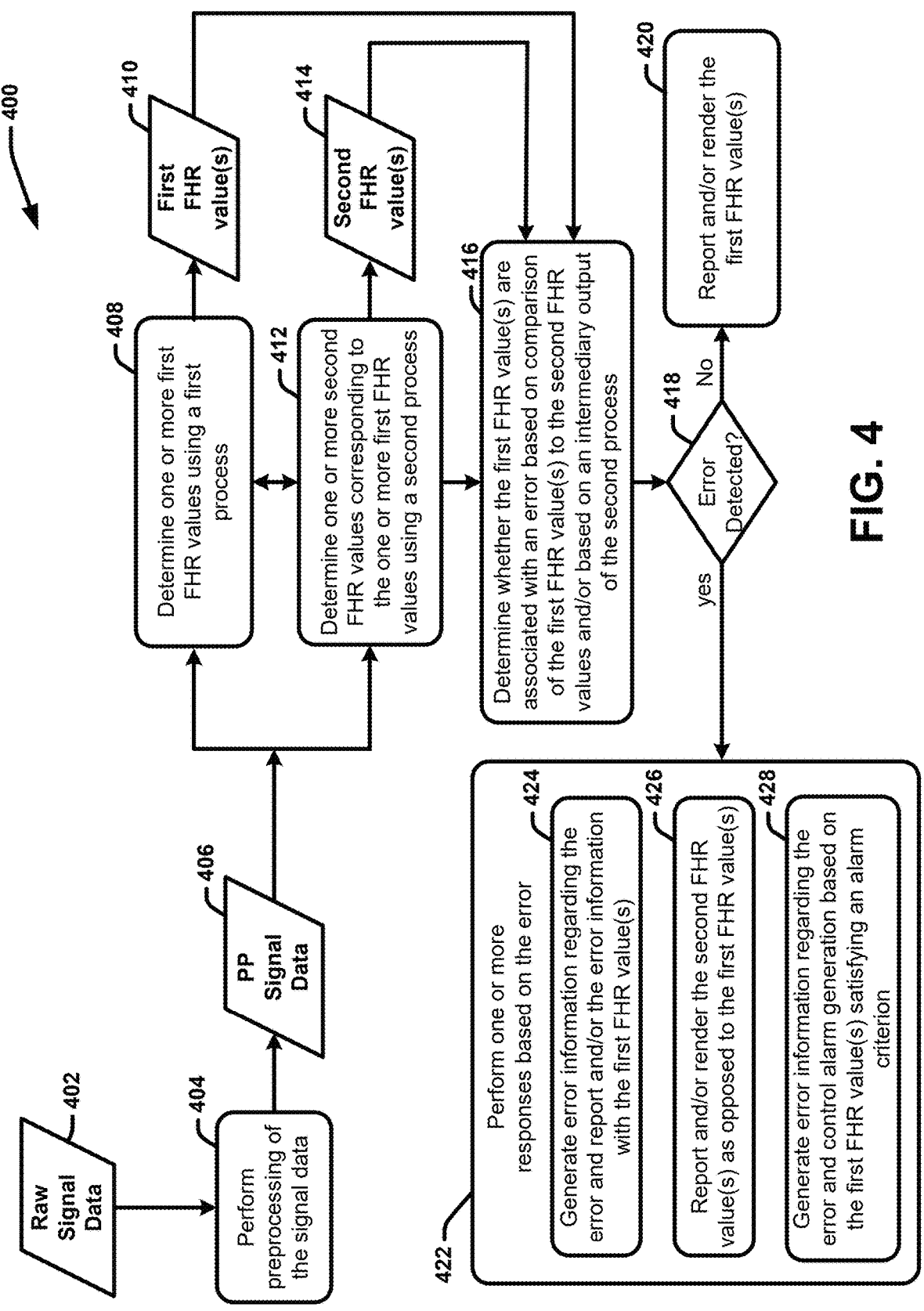
FIG. 4 presents a flow diagram of an example real-time doppler ultrasound signal processing process for fetal heartbeat detection with supervisory error control, in accordance with one or more embodiments of the disclosed subject matter.

In this regard, FIG. 4 presents a flow diagram of an example real-time doppler ultrasound signal processing process 400 for fetal heartbeat detection with supervisory error control, in accordance with one or more embodiments of the disclosed subject matter. With reference to FIGS. 1-4, process 400 corresponds to a real-time signal processing process that can be performed by signal processing component 202 (and/or master signal processing component 306) in accordance with one or more embodiments.

In accordance with process 400, raw signal data 402 as captured via the ultrasound transducer 238 is received/acquired by the signal processing component 202 (and/or the master signal processing component 306) in real-time over the course of a fetal monitoring session. The raw signal data 402 corresponds to the raw doppler-shifted ultrasound signals captured/received by the ultrasound transducer 238 over time. In this regard, the raw signal data 402 corresponds to a real-time stream of raw doppler-shifted ultrasound signals as captured/received by the ultrasound transducer 238 in real-time over the course of the fetal monitoring session. To this end, process 400 corresponds to a continuous process that involves continually receiving new raw signal data 402 over time and performing the processing functions described repeatedly and in real-time as applied to the new signal data as it is received over time.

At 404, the preprocessing component 204 can perform preprocessing of the signal data 402 to transform the raw signal data 402 into preprocessed (PP) signal data 406 as the raw signal data 402 is received (i.e., in real-time). In this regard, the raw signal data 402 received by the ultrasound transducer 238 generally represents the frequency and intensity or amplitude of ultrasound signals received by the ultrasound transducer as reflected off moving structures such as the fetal heart and recorded over time. The raw signal data 402 corresponds to a digitized representation of the frequency and intensity of the received signals over time and is represented graphically as a waveform. To this end, the raw signal data 402 and the PP signal data 406 respectively correspond to continuous waveform data that represents the frequency and intensity of the received signals over time and in real-time. The received raw signal data 402 is a modulated signal, meaning its amplitude varies rapidly due to the motion of the fetal heart. In addition, the raw signal data 402 can be affected by various sources of noise, including electrical interference, maternal movements, or artifacts. The preprocessing performed at 404 (e.g., via preprocessing component 204) is used to enhance the accuracy and reliability of the FHR assessment therefrom by the primary FHR estimation component 206 at 408 and the supervisory FHR assessment component 210 at 412.

In various embodiments, the preprocessing performed at 404 (e.g., via preprocessing component 204) can include demodulation, noise filtering and smoothing of the raw signal data 402 to transform the raw signal data 402 into PP signal data 406 that has been demodulated, noise filtered and smoothed. Demodulation is the process of extracting the low-frequency doppler shift from the high-frequency modulated signal. Noise filtering refers to the removing unwanted noise from the raw signal data 402. In some embodiments, the noise filtering techniques performed at 404 can include performing an envelope detection process to outline the raw waveform of the raw signal data 402. The envelope detection process involves isolating the slow-varying changes in the raw signal data 402, essentially outlining the raw waveform. The resulting waveform from the envelope detector may still contain rapid fluctuations, known as ripple or noise. To obtain a smoother representation of the envelope detector output, the preprocessing component 204 can also apply a smoothing function to the outlined waveform data, such as a low-pass filter, to remove high-frequency components, leaving the slower-varying changes. The resulting PP signal data 406 corresponds to filtered and refined waveform data that reflects the frequency and amplitude of the signals received/detected by the ultrasound transducer 238 as a function of time.

The resulting PP signal data 406 is then used as input at 408 and 412. In this regard, at 408 the primary FHR estimation component 206 determines one or more first FHR values 410 (e.g., in real-time) based on processing the PP signal data 406 using a first process. The PP signal data 406 is also used as input at 412, wherein the supervisory FHR estimation component 210 determines one or more second FHR values 414 corresponding to the one or more first FHR values 410 using a second process, different from the first processes. Of particular importance, in accordance with process 400, processing of the PP signal data 406 using the first process performed at 408 (e.g., via the primary FHR estimation component 206) and the processing of the PP signal data 406 performed at 412 using the second process (e.g., via the supervisory FHR estimation component 206) is performed simultaneously and/or in parallel. In this regard, the preprocessing component 204 provides duplicate streams of the PP signal data 406 to the primary FHR estimation component 206 and those components involved in the second process (e.g., windowing component 208, supervisory FHR estimation component 206, pattern assessment component 212, and other, as described below). As shown in FIG. 4, the output of the first process performed at 408 can include one or more first FHR values 410 as determined based on the PP signal data 406, and the output of the second process performed at 412 can include one or more second FHR values 414 corresponding to the one or more first FHR values.

In various embodiments, the first process employed by the primary FHR estimation component 206 to determine the one or more first FHR values 410 at 408 can include or correspond to an autocorrelation process. Autocorrelation involves comparing the doppler signal with a time-delayed version of itself. In its simplest form, the autocorrelation function is calculated by sliding the doppler signal over itself at different time lags and measuring the similarity at each lag. The autocorrelation function examines peaks at time lags corresponding to the periodicity of the fetal heartbeats. In this regard, when the Doppler ultrasound beam detects the movement of tissues such as the fetal heart the transducer, it produces a peak in the signal waveform corresponding to the raw signal data 402. This occurs because the frequency of the returning ultrasound waves changes due to the Doppler effect. The height of the peaks in the doppler waveform corresponds to the amplitude or intensity of the received signal. The distance between consecutive peaks corresponds to the time interval between heartbeats, allowing for the estimation of the fetal heart rate. The time lag associated with the highest peak in the autocorrelation function represents the duration of one fetal heartbeat. The autocorrelation function estimates the FHR by calculating the reciprocal of this duration.

However, the doppler-signal waveform data can exhibit complex and variable patterns attributed to both signals of interests (e.g., fetal heartbeats) as well as other signals such as noise and artifacts, which makes distinguishing between peaks corresponding to actual fetal heartbeats difficult. Autocorrelation based algorithms can be sensitive to noise and limited in their ability to adapt to variations in signal characteristics due to fetal movement and other physiological factors. These constraints may result in false interpretations of the FHR, particularly with respect to the HC/DC problem. In particular, the raw signal data 402 and the PP signal data 406 generally consists of a lub peak corresponding to the diastole movement of the fetal heart and a dub peak corresponding to the systole movement of the fetal heart. The lub to dub distance of a fetal heart and the ratios of the amplitudes of both can vary drastically from one fetus to another. Due to the sensitivity of the autocorrelation function, when the FHR drops to low values (e.g., less than about 120 BPM), the autocorrelation algorithm can interpret both the movements of the heart (diastole-systole) as beats, effectively giving a much higher FHR value than the ground truth (generally double, hence referred to a double counting). Likewise, when the FHR increases to about 180 BPM or greater, the movements become close enough together that a couple of the beats get clumped together by the autocorrelation function and interpreted as a single beat, thus the FHR value drops to half the value (i.e., half counting).

Figure 5A:
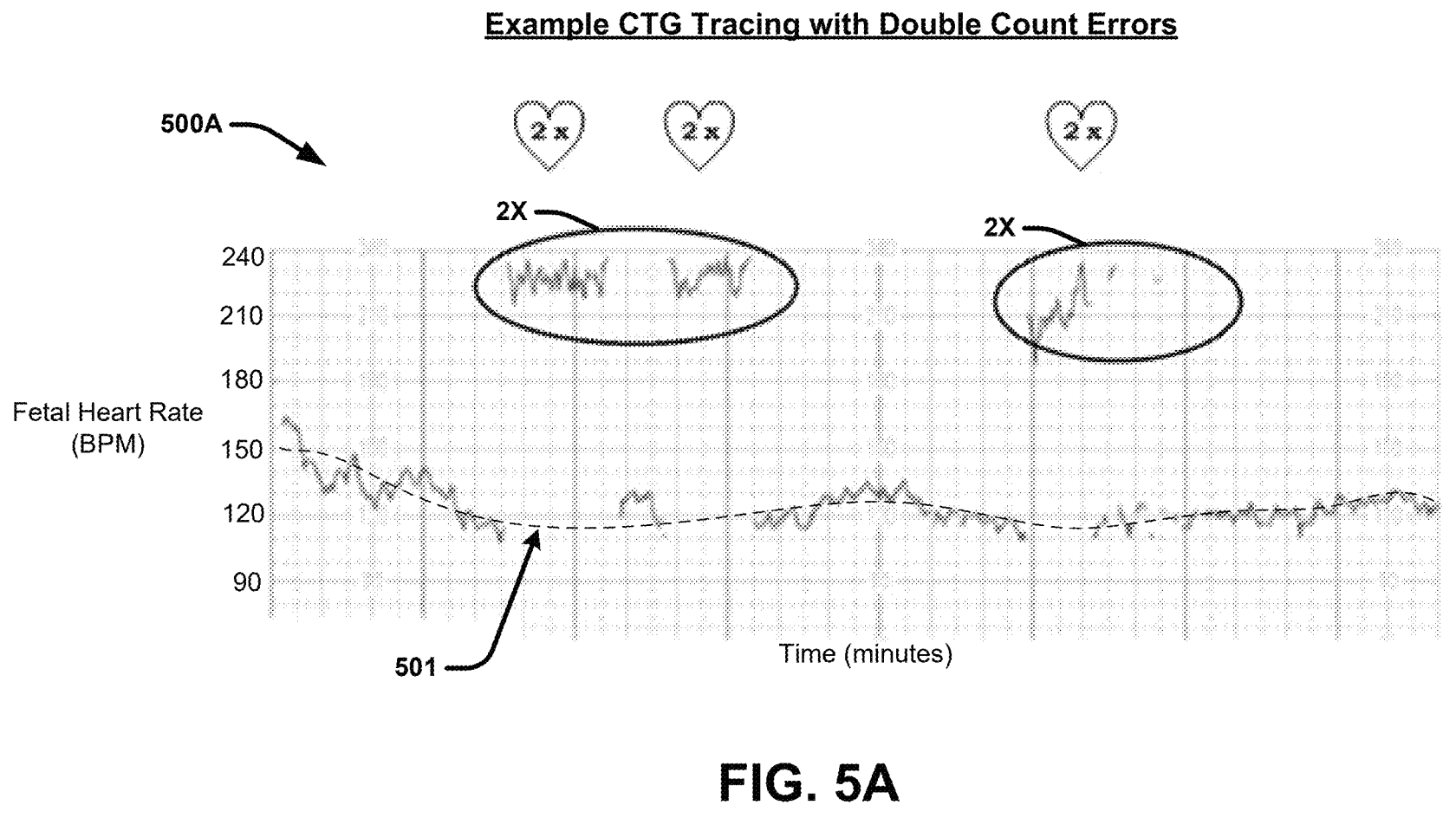
Figure 5B:
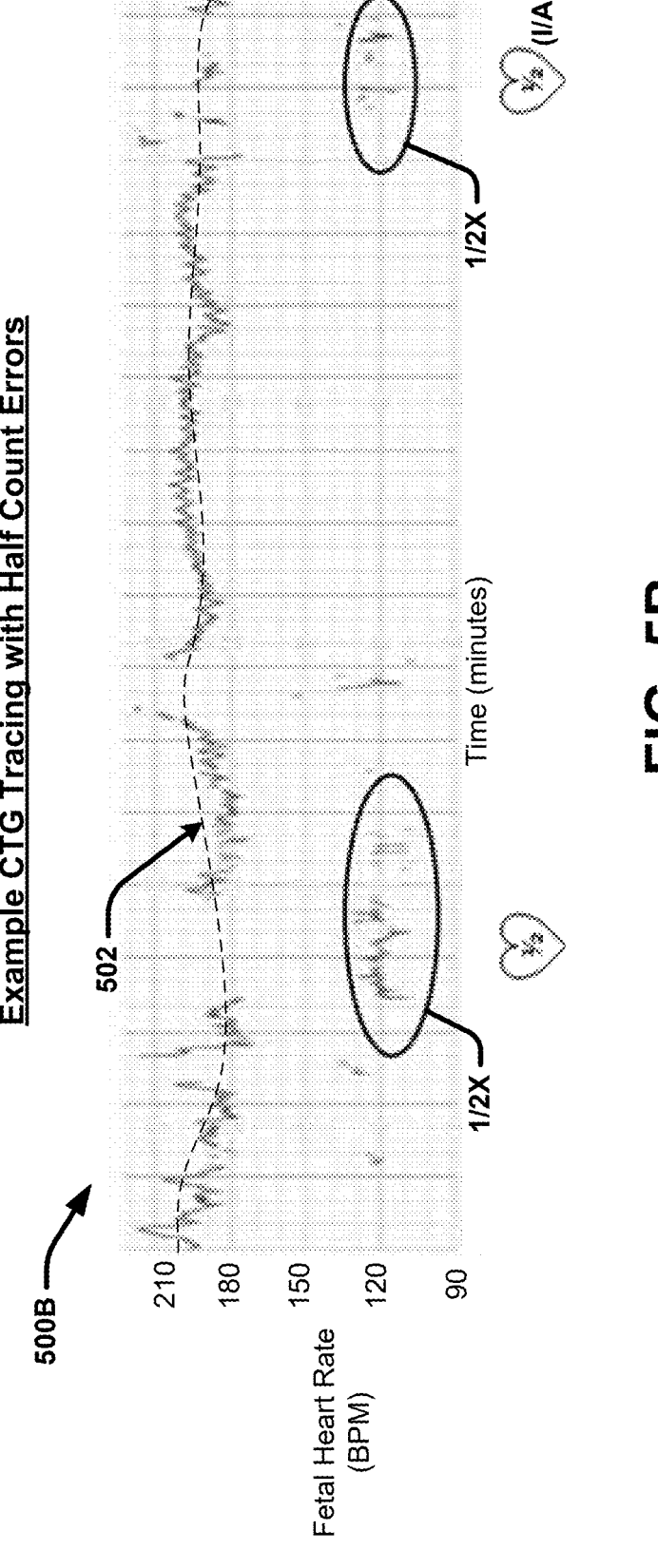
FIG. 5B presents an example cardiotocography tracing comprising half-count errors, in accordance with one or more embodiments of the disclosed subject matter.

In this regard, FIG. 5A presents an example CTG tracing 500A comprising example double-count errors (encircled and indicated with the 2X indica), in accordance with one or more embodiments of the disclosed subject matter. FIG. 5B presents another example CTG tracing 500B comprising example half-count errors (encircled and indicated with the ½× indica), in accordance with one or more embodiments of the disclosed subject matter. With reference to FIGS. 1-5B, both CTG tracing 500A and CTG tracing 500B provide a graphical representation of the first FHR values 410 (in BPM) plotted over a period of time of a fetal monitoring session, with each line along the x-axis corresponds to a single minute and respective lines along the y-axis represent the FHR values. CTG tracing 500A and CTG tracing 500B correspond to output data that is typically generated and rendered to clinicians (noting however, minus the DC/HC indications illustrated) via a display monitor (e.g., via monitor device 102) and/or a printed strip over the course of a fetal monitoring session. In addition to the graphical CTG tracing data, the FMS may also display a numerical value of the current FHR and/or the baseline FHR as updated in real-time. In various embodiments, the monitor device 102 can be configured to render either or both of these types of output data over the course of the monitoring session, and/or additionally types of output data discussed herein (e.g., output data identifying or indicating HC/DC errors, detected artifacts, signal quality, repositioning indications, alarms, notifications, etc.).

In CTG tracing 500A, the FHR pattern 501 following the dashed line represents the FHR baseline, which in this example is around 120 BPM. The shifts encircled represent instances of double counting, where the first FHR values 410 determined over the corresponding periods of minutes by the first process, at around 240 BPM, correspond to significantly higher values relative to the baseline FHR value (i.e., essentially double the baseline FHR value and thus double counting). CTG tracing 500A includes three instances of double counting over the period of time represented.

Half counting of high BPM signals would normally happen at high BPM's where couple of beats close by are interpreted as one or due to low SNR's where the alternate peaks get missed by the autocorrelation algorithm and the eventual output is a very low BPM value as compared to the ground truth, as illustrated in FIG. 5B and CTG tracing 500B. For example, in CTG tracing 500B, the FHR pattern 502 following the dashed line represents the FHR baseline value, which in this example is around 210 BPM. In this example, the shifts encircled represent instances of double counting, where the first FHR values 410 determined over the corresponding periods of minutes by the first process, at around 120 BPM, correspond to significantly lower values relative to the baseline (e.g., essentially half the baseline FHR value and thus half-counting). In this example, there are two instances of half counting over the period of time represented.

With reference back to process 400, in order to detect errors associated with the first FHR values 410, such as HC errors, DC errors, and/or the false or otherwise inaccurate first FHR values 410, process 400 incorporates two different parallel processes (e.g., performed simultaneously and/or in parallel) for determining the FHR values, that is the first process performed at 408 and the second process performed at 412. As noted above, the first process can include or correspond to one or more autocorrelation processes. Different from the autocorrelation process, in various embodiments, the second process performed at 412 can include or correspond to a windowing process that comprises dividing the input PP signal data 406 into consecutive signal data segments as a function of a windowed time interval as the PP signal data 406 is received (e.g., via windowing component 208), and separately evaluating each segment of the consecutive signal data segments as they are generated in association with detecting signal peaks within each segment corresponding to heartbeats of the fetal heart being targeted by the ultrasound transducer 238.

More particularly, in one or more embodiments, the windowing process can incorporate one or more peak detection algorithms that facilitate detecting individual peaks included within each of the segments corresponding to individual heartbeats. To this end, in accordance with the windowing process, the windowing component 208 divides the PP signal data 406 into consecutive signal data segments as a function of a defined window of time (i.e., a windowed time interval) as the signal data is received in real-time. For example, let's assume the duration of the defined window of time is 4 seconds. In accordance with this example, each signal data segment will comprise PP signal data corresponding to a different 4 second period of time, and each signal data segment will be generated consecutively or sequentially over time. At 412, as each segment of signal data is generated, the supervisory FHR estimation component 210 performs a peak detection process to identify one or more peak included in the segment respectively corresponding to a fetal heartbeat, or determines, as a result of the peak detection process, that the segment does not comprise any peaks corresponding to a fetal heartbeat.

At 412, the supervisory FHR estimation component further tracks the number of fetal heartbeats detected within a set of signal data segments received/generated over every defined period of time, such as every one minute (as applied to calculating a second FHR value as function of the set in BPM). For instance, in accordance with the example in which each signal data segment is 4 seconds, and the defined period of time is 60 seconds (i.e., one minute), each set of signal data segments will include 15 separate segments. To this end, at 412 the supervisory FHR estimation component determines the one or more second FHR values 414 based on the number of fetal heartbeats detected for a portion of the PP signal data 406 received over a current period of time (e.g., the most recent one minute period or another defined period of time). Importantly, at 408 the primary FHR estimation component 206 processes the same portion of the PP signal data 406 in parallel with the supervisory FHR estimation component 210 in association determining the one or more first FHR values 410. In other words, both the primary FHR estimation component 206 and the supervisory FHR estimation component 210 process the same signal data in association with determining one or more FHR values based thereon, yet using different processing algorithms. In this manner, differences between the outputs of the first and second processing algorithms can be used to detect errors.

Figure 6A:
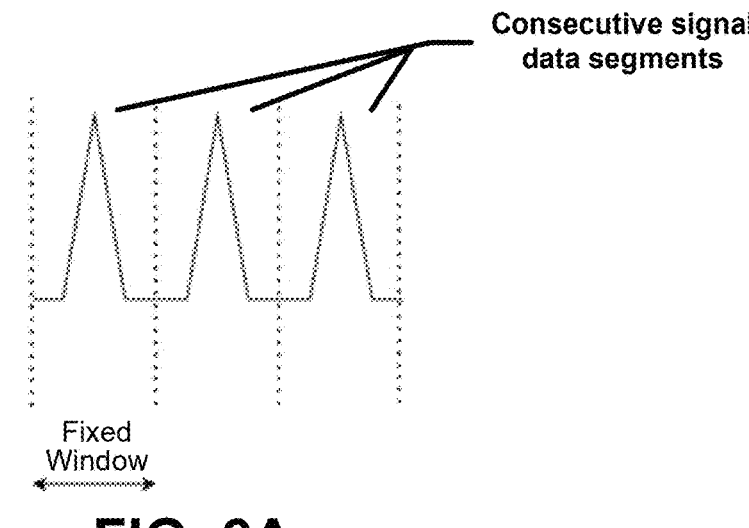
FIG. 6A illustrates aspects of a fixed windowing process for FHR detection, in accordance with one or more embodiments of the disclosed subject matter.

In some embodiments, the windowing process can include or correspond to a fixed windowing process wherein the duration of the defined windowed time interval used by the windowing component 208 to generate the consecutive segments of the PP signal data 406 is fixed over the duration of the fetal monitoring session. With these embodiments, the windowing component 208 repeatedly divides the PP signal data 406 into consecutive signal data segments having the same, fixed duration over the course of the fetal monitoring session, as illustrated in FIG. 6A. The duration of the fixed windowed time interval can vary and be tailored based on various factors, such as the operating parameters of the ultrasound transducer 238, the baseline FHR, and other contextual factors. In various embodiments, the fixed duration of the windowed time interval can range from about 250 microseconds (μs) to about 2.0 seconds. Ideally, the duration of the fixed window is set to result in a single peak included within each windowed segment corresponding to a single heartbeat. However, with these embodiments, depending on the duration of the fixed window and the actual heart rate of the fetus, the number of peaks corresponding to individual heartbeats included within each window may vary and include one or more peaks corresponding to one or more heartbeats.

Figure 6B:
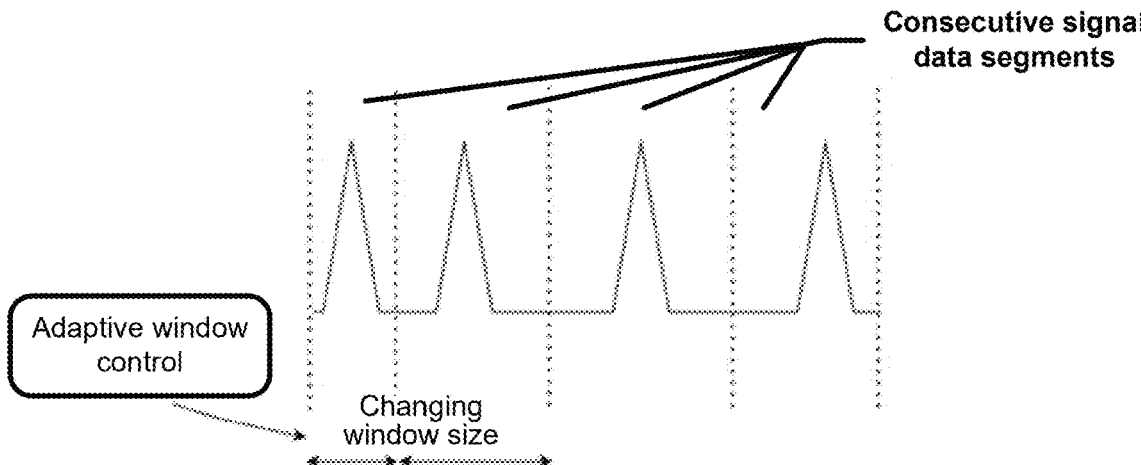
FIG. 6B illustrates aspects of an adaptive windowing process for FHR detection, in accordance with one or more embodiments of the disclosed subject matter.

Additionally, or alternatively, the windowing process can include or correspond to an adaptive windowing process wherein the windowing component 208 varies and adapts the duration of the windowed time interval over the course of the fetal monitoring session, with the goal of tailoring the size of each window to include a single peak corresponding to a single heartbeat, as illustrated in FIG. 6B. In FIG. 6B, four consecutive signal segments respectively have different windowed durations, indicating the windowing component 208 can adapt and tailor the duration of the windowed time interval in real-time for every signal segment generated. To this end, the rate at which the windowing component 208 adapts the duration of the windowed time interval defining the duration of each signal data segment can vary, and be as frequently as every instance of generation of signal data segment or greater (e.g., as a function of number of consecutive signal data segments and/or time). In some embodiments, to facilitate this end, windowing component 208 can determine and control the size (i.e., the duration) of the respective signal data segments in real-time based on data generated via the parallel/simultaneous performance of the first process (e.g., at 408) in association with processing the same portion of the corresponding PP signal data. More particularly, in embodiments in which the first process corresponds to an autocorrelation process, the windowing component 208 can use one or more parameters determined in accordance with the autocorrelation process to determine an appropriate window size or duration of one or more of the consecutive signal data segments for a current period of time. For example, the one or more parameters can include but are not limited to, a first FHR value of the one or more first FHR values 410 and/or a distance between two peaks determined via the autocorrelation process.

Additionally, or alternatively, in accordance with the adaptive windowing process, the windowing component 208 can determine and control the size (i.e., the duration) of the respective signal data segments in real-time based on the baseline FHR, and/or one or more previous first FHR values and/or peak to peak distance values determined by the primary FHR estimation component 206 at 408 based on preceding signal data (e.g., PP signal data 406) received and processed prior to the current signal data being processed in real-time at 408 (e.g., the immediately preceding portion of the PP signal data 406). In this regard, the time between heartbeats, and thus the distance between corresponding peaks corresponding to heartbeats, is inversely proportional to the FHR, wherein as the FHR decreases the distance increases, and as the FHR increases the distance decreases. Thus, in some implementations, the windowing component 208 can control the duration/size of the respective signal data segments as a function of one or more of the most recent past first FHR values (and/or an average thereof) using a window sizing function that increases the window size as the one or more past first FHR values decreases and decreases the window size as the one or more past first FHR values increases.

In accordance with one or more embodiments of the adaptive windowing process, in association with separately evaluating each segment of the consecutive signal data segments, the supervisory FHR estimation component 210 can be configured to either identify only a single peak included in the segment corresponding to a fetal heartbeat, or no signal peaks included in the segment corresponding to the fetal heartbeat.

Additionally, or alternatively, the windowing process can include or correspond to a pattern classification process, wherein as opposed to (and/or in addition to) detecting only one or more peaks included within each of the signal data segments corresponding to a fetal heartbeat (or lack thereof), the supervisory FHR estimation component 210 can use pattern recognition (e.g., as facilitated via pattern assessment component 210) to identify and classify distinct patterns observed within the signal data segments corresponding to known or learned waveform patterns corresponding to heartbeats of the fetus being monitored. With these embodiments, the windowing component 208 can apply the fixed duration for the windowed time interval (e.g., such that every segment has the same duration or window of time). For example, the pattern classification process can involve classifying ultrasound doppler 1D signals into "n" patterns and then identifying the patterns in real-time by either template matching or mapping them to potentially identified peaks/beats in the input signal data. This can involve identifying and classifying the distinct patterns as separately included within the respective signal data segments as divided into segments of the same, fixed duration, and correlating the distinct patterns to occurrences of fetal heartbeats (e.g., as determined based on the output of the peak detection algorithm employed by the supervisory FHR estimation component 210 for the corresponding portion of signal data in accordance with the fixed windowing processes discussed above and/or as determined based on one or more outputs of the first process employed by the primary FHR estimation component 206 in association with simultaneously processing the same corresponding portion of the PP signal data 406). In association with correlating the distinct patterns to occurrences of fetal heartbeats, the pattern assessment component 212 can also correlate the distinct patterns to one or more other parameters associated with the fetal heartbeats and the corresponding segment of the PP signal data 406, such as peak intensity/amplitude, distance between lub and dub peaks, ratio of the amplitude of the lub to dub peaks, SNR of the corresponding portion of the signal data, and other parameters.

Figure 6C:
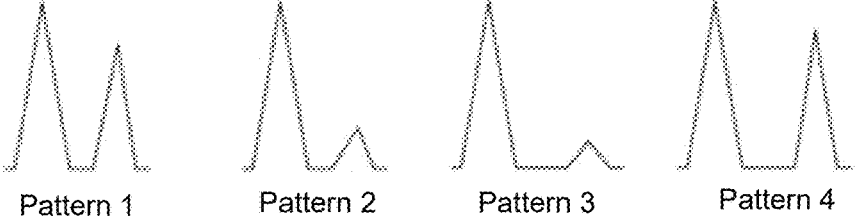
FIG. 6C illustrates aspects of pattern classification in association with FHR detection, in accordance with one or more embodiments of the disclosed subject matter.

For example, FIG. 6C illustrates four different waveform patterns respectively corresponding to fetal heartbeats respective associated with signal data segments of the same duration (e.g., 2 seconds or less). Each of the distinct patterns include two peaks, respectively corresponding to a lub peak (diastole movement) and a dub peak (systole movement). The lub to dub distance of a fetal heartbeat and the ratios of the amplitudes of both can vary drastically from one fetus to another and the operating context of the fetal monitoring session (e.g., operating parameters of the ultrasound transducer 238, fetal position/depth, signal quality, and other parameters). Accordingly, the particular lub-dub peak waveform pattern or patterns for each fetus and each monitoring session can vary.

Accordingly, in some embodiments, the pattern assessment component 212 can identify one or more distinct patterns observed in signal data segments (of the same, fixed duration), received/generated over a first period of time (e.g., a few minutes or another suitable period of time) of the fetal monitoring session (e.g., a calibration period) and correlate or classify the one or more distinct waveform patterns into fetal heartbeat representations using one or more classification algorithms, correlation algorithms, machine learning algorithms or the like. With these embodiments, the pattern classification process can involve using the fixed windowing described above, wherein the pattern assessment component 212 classifies the distinct waveform patterns as observed within fixed windowed time intervals. The fetal heartbeat representations can include or correspond to reference information that correlates each distinct pattern as a fetal heartbeat occurrence and optionally defines parameters associated with each pattern, such as but not limited to, the corresponding window size within which they were observed (e.g., in implementations in which the windowing component 208 determines the fixed window size during the calibration period), peak intensity/amplitude, distance between lub and dub peaks, ratio of the amplitude of the lub to dub peaks, SNR of the corresponding portion of the waveform data, and other parameters.

Clinically, the most reliable time period for the pattern assessment component 212 to classify the distinct pattern or patterns of the doppler waveform can include a timeframe at which the FSD 104 has been positioned on the mother at a final position relative to a fetal heart being monitored (and no longer being moved about the mother) and at which the heart rate of the fetal heart is being accurately and consistently detected. For example, this timeframe can occur at the beginning of the monitoring session after the clinician has completed placement of the FSD 104 and ensured no false FHR values are being observed. Thus, in some implementations, the pattern assessment component 212 can be configured to activate the first time period at this time and complete defining the fetal heartbeat representations once convergence is reached (e.g., once additional new patterns are no longer observed). An alternate timeframe for performing pattern classification can include a timeframe when the FHR baseline values are within the "normal' range (e.g., as predefined via upper and lower thresholds, such as between 120 BPM and 180 BPM, or more preferably between 130 and 170 BPM) and well outside the boundary regions (e.g., less than 120 BPM and greater than 180 BPM)

where the typical half count and double count scenarios are observed. Thus, additionally or alternatively, the pattern assessment component 212 can be configured to perform pattern classification over one or more periods of time in which the FHR baseline values are within the normal range. Still in other embodiments, the pattern assessment component 212 can use the SNR of the input signal as a metric for determining when to perform pattern classification. For example, the pattern assessment component 212 can be configured to perform pattern classification when the SNR of the signal is above a defined threshold indicating that the signal quality is strong and well enough to perform pattern classification.

After the pattern assessment component 212 has identified and classified the one or more distinct patterns into defined fetal heartbeat representation over the first period, the supervisory FHR estimation component 210 can employ the pattern assessment component 212 and the fetal heartbeat representations to identify and classify the distinct patterns as they are observed in the consecutive signal data segments for the remainder of the fetal monitoring session and/or for any additional period of time (e.g., a second period of time) over the course of the fetal monitoring session in real-time (e.g., either via template matching or mapping them to potentially identified peaks/beats in the FHR signal). In this regard, the supervisory FHR estimation component 210 can employ the pattern assessment component 212 to identify the distinct patterns observed in the consecutive signal data segments over a second period of the time after the first period of time and classify them as occurrences of fetal heartbeats in association with determining the one or more second FHR values and/or in association with determining whether the corresponding ones of the first FHR values are associated with an error. This can include identifying the distinct patterns as they are observed within the signal data segments to determine whether each signal data segment includes a fetal heartbeat or not in association with tracking occurrences of fetal heartbeats over a time.

In some embodiments, at 412 the supervisory FHR estimation component 210 can employ a combination of two or more of the above noted windowing processes and the pattern classification process to determine the second FHR values. In other embodiments the supervisory FHR estimation component 210 can dynamically switch between different windowing processes (e.g., fixed windowing, adaptive windowing) and/or the pattern classification process over the course of the monitoring session based on monitored characteristics of the FHR, the SNR of the signal and other factors, as appropriate and in accordance with a defined FHR estimation protocol.

Continuing with process 400 in view of FIGS. 1-6C, at 416, the error detection component 214 can determine whether the one or more first FHR values 410 are associated with an error (e.g., a false or spurious value, a half count error, or a double count error) based on comparison of the one or more first FHR values 410 to the corresponding one or more second FHR values respectively determined via the first and second processes based on the same portion of the PP signal data 406 (corresponding to the same time period, such as one minute as applied to a single FHR value measured in BPM, or longer as applied to a plurality of FHR values measured in BPM), and/or based on an intermediary output of the second process.

In this regard, in some embodiments, the error detection component 214 can determine whether one or more first FHR values 410 are associated with an error based on differences between the one or more first FHR values 410 and the corresponding one or more second FHR value 414 relative to one or more defined error criteria for the differences. In some implementations, these embodiments can only be applied when fixed windowing is used. For example, the error detection component 214 can classify a first FHR value as being a false value based on the difference between the first FHR value and the corresponding second FHR value exceeding a defined threshold amount. The error detection component 214 can also determine the type of the error (e.g., an HC error, a DC error, or a false value that does not correspond to an HC/DC error) based on the degree and direction of the difference. For example, the error detection component 214 can determine whether a false first FHR value corresponds to a HC error based on whether the first FHR value is less than the second FHR value and the degree or amount of the difference being greater than about 40%, 45% or the like (e.g., essentially half or near 50%). Likewise, the error detection component 214 can determine whether a first FHR values corresponds to a DC error based on whether the first FHR value is greater than the second FHR value and the degree or amount of the difference being greater than about 100%, or the like (e.g., essentially double). To this end, the error detection component 214 can classify other first FHR values as being false values that do not correspond to HC or DC instances, but still deviate from the corresponding second FHR values by an amount determined to be clinically relevant, as defined based on one or more difference amount thresholds.

In some implementations of these embodiments, the error detection component 214 can also consider the number of first FHR values determined to be false (as well as their error type) detected within a defined timeframe (e.g., greater than 1 minute) in association with determining whether to classify the first FHR values as being associated with an error. In this regard, HC/DC scenarios often involve several consecutive abnormally low/high FHR value outputs via the autocorrelation algorithm. For instance, in accordance with the examples illustrated in FIGS. 5A and 5B, both the three instances of the DC errors and the two instance of HC errors involved a period of several minutes over which the several consecutive first FHR values remained essentially twice and half the baseline values respectively. In this regard, the frequency and/or repetition rate of consecutive first FHR values over a period of time (e.g., 2-5 minutes for instance) deviating from the corresponding second FHR values can also be used as a factor in association with detecting and classifying errors. For example, the error detection criteria employed by the error detection component 214 may direct the error detection component 214 to only classify occurrence of an HC or DC error after detecting two consecutive first FHR values meeting the HC or DC error criteria.

Additionally, or alternatively, as applied to the adaptive windowing process, the error detection component 214 can determine whether one or more first FHR values 410 are associated with an error based on an intermediary output of the second process. With these embodiments, the intermediary output corresponds to the number of heartbeats detected within each segment of the consecutive segments. In this regard, as noted above, in accordance with the adaptive windowing process, the windowing component 208 can tailor the duration of the respective segments such that each segment should only include a single peak corresponding to a single fetal heartbeat. For example, the windowing component 208 can use one or more of the first FHR values 410 determined by the primary FHR estimation component 206 at 408 to define the window size/duration for the segments evaluated at 412. For example, the windowing component 208 can define the window size based on a first FHR value determined at 408 based on a current portion of the PP signal data 406 and the windowing component 208 can divide the same, current portion of the PP signal data 406 evaluated at 412 into segments according to a window size/duration based on the first FHR value. Additionally, or alternatively, the first FHR value used to define the window size/duration for the segments evaluated at 412 can correspond to a previous determined first FHR value, such as the last, most recent first FHR value determined based on the last, most recent portion of the PP signal data 406 evaluated at 408.

In either of these implementations, given a first FHR value determined at 408, the windowing component 208 can set the duration/size of the segments based on the first FHR value such that each segment should include a single peak corresponding to a single heartbeat. For instance, if the first FHR value is 60 BPM, then the window size/duration can be set to 1.0 second in association with evaluating a 1.0 minute portion of the PP signal data 406 at 412 to generate 60 segments, each having a 1.0 second duration, with the assumption that each segment evaluated at 412 should include one signal peak corresponding to one heartbeat. In accordance with this example, if one or more of the segments includes two signal peaks corresponding to two heartbeats, this indicates that the first process missed counting a heartbeat and thus the 60 PBM value is associated with a half count (HC) error. To this end, a true HC error would correspond to all of 60 segments including two signal peaks. Thus, the greater number of segments including two peaks, the higher the probability that the first FHR value is associated with a HC error. Likewise, if one or more of the segments does not include any signal peaks, this indicates that the first FHR values is associated with a double count error, with a true double count error corresponding to every alternate segment missing a signal peak corresponding to a heartbeat.

Thus, in accordance with the adaptive windowing process, the error detection component 214 can determine whether a particular segment is associated with a HC error based on the segment having two peaks corresponding to two heartbeats. Likewise, the error detection component 214 can determine whether a particular segment is associated with a double count error based on the segment having no signal peaks corresponding to a fetal heartbeat. In some implementations, in response to detection of a segment having two peaks corresponding to two heartbeats, the error detection component can generate a HC error warning (which can be reported and rendered in real-time). Likewise, in response to detection of a segment having no peaks corresponding to a fetal heartbeat, the error detection component 214 can generate a double count error warning (which can be reported and rendered in real-time). Still in other embodiments, the error detection component 214 can determine occurrences of HC and DC errors based on a number of consecutive or non-consecutive segments having double or no heartbeat peaks respectively, within a defined timeframe exceeding a threshold number (e.g., three, five, ten, or another suitable number). To this end, the defined timeframe can be less than one minute.

If at 418 the error detection component 214 determines that no errors are observed, then process 400 can continue to 420, wherein the FMS 100 can report (e.g., via the FSD 104 to the monitor device 102 using reporting component 226) and/or render (e.g., via the monitor device 102 and rendering component 302) the first FHR values and/or information identifying or indicating the first FHR values (e.g., graphical data, audible data, printed data, etc.) in accordance with normal operation.

However, if at 418 the error detection component 214 determines that one or more of the first FHR values 410 are associated with an error, then process 400 can continue to 422, wherein the FMS 100 can perform one or more responses based on the error. Of particular importance, because process 400 corresponds to a real-time process in which the errors are detected in real-time based on the current portion of the stream of PP signal data 406, the one or more responses correspond to real-time responses that involve alerting clinicians regarding the identified errors in real-time as they are observed and/or, correcting the errors in real-time (e.g., on the fly) and/or minimizing alarm fatigue in real-time. In this context, the term "real-time" reflects an update rate of every defined time period, such as every one minute as applied to generating an updated FHR value via the first process and the second process every minute as measured in BPM, or another defined time period.

In this regard, in some embodiments, the one or more responses can include (at 424) generating error information (e.g., via the error detection component 214) regarding the error and reporting (e.g., via reporting component 226) and/or rendering (e.g., via rendering component 302) the error information with the first FHR values 410 and/or information indicating the first FHR values. For example, in some implementations, the error information can identify the type of the error (e.g., a false value, an HC error, a DC error, etc.) and the particular portion of the CTG tracing data comprising the error, and/or the particular rendered FHR values having the error. The format of the error information and the manner in which the error information is rendered via the monitor device 102 (e.g., via rendering component 302) can vary. In one example, as illustrated with reference to FIGS. 5A and 5B and the corresponding CTG tracings 500A and 500B, the rendering component 302 can generate and/or render the error information as visual error data incorporated on or within the CTG tracing rendered via the monitor device 102 (e.g., via a display monitor and/or a printed strip) in real-time as the errors are detected. For instance, as illustrated in FIG. 5A, CTG tracing 500A includes visual markings encircling the FHR values associated with the DC errors and/or indica (e.g., 2× indica associated with the markings and heart symbols with the 2× indica there above indicating a DC error corresponding to the encircled FHR values). Similarly, as illustrated in FIG. 5B, CTG tracing 500B includes visual markings encircling the FHR values associated with the HC errors and/or indica (e.g., ½× indica associated with the markings and heart symbols with the ½× indica there below indicating a HC error corresponding to the encircled FHR values). These visual markings correspond to example error information that may be generated and rendered via the error detection component 214 and/or the rendering component 302 based on detection of corresponding HC and DC errors in accordance with the disclosed techniques. In another example, the rendering component 302 and/or the alarm generation component 308) can generate and/or render the error information as audible data in the form of an audible signal that indicates occurrence of the error and/or the type of the error (e.g., either HC or DC).

Additionally, or alternatively, the one or more responses can include at 426, reporting and/or rendering the one or more second FHR values 414 (i.e., the correct values) corresponding to one or more first FHR values 410 associated with the error as opposed to reporting and/or rendering the one or more first FHR values 410 (e.g., thereby correcting the errors on the fly). With these implementations, the rendering component 302 can control the FHR information rendered via the monitor device 102 (e.g., CTG tracing data, digital FHR values, audible data, etc.) to ensure the FHR information does not reflect FHR values corresponding to false values.

Additionally, or alternatively, the one or more responses can include at 428, generating error information regarding the error (e.g., via error detection component 214) and controlling alarm generation based on the one or more first FHR values 410 satisfying (or more particularly falsely satisfying) an alarm criterion (e.g., via alarm generation component 308 and/or alarm control component 310). In this regard, in some embodiments, the alarm generation component 308 and/or a similar component executed by an external system communicatively coupled to the monitor device 102, such as a global monitor in the NICU or the like) can be configured to generate alarms based on the heart rate of a monitored fetus being indicative of a possible clinical complication or condition warranting clinical intervention or acknowledgment. This can include the heart rate dropping to a clinically significant low value (e.g., relative to one or more minimum thresholds) and/or increasing to a clinically significant high value (e.g., relative to one or more maximum thresholds). False alarm generation by fetal monitoring systems such as FMS 100 is a significant problem wherein false alarms are generated based on invalid FHR values indicating an abnormally low or high FHR as a result of one or more HC or DC errors. Thus, in some embodiments, the alarm control component 310 can control or regulate alarm generation by the alarm generation component 308 (and/or an external system/device) in response to the one or more first FHR values (falsely) satisfying an alarm criterion (e.g., being too high or too low relative to defined thresholds) based on the one or more first FHR values being associated with a DC or HC error. For example, in some implementations, based on the one or more first FHR values being associated with a DC or HC error and thus resulting in them being (falsely) abnormally high or low, the alarm control component 310 can prevent generation of a corresponding alarm, thereby minimizing alarm fatigue. In another example, the alarm control component 310 can assign lower priorities to the same and optionally dismiss them once the HC/DC instance has passed.

In some embodiments, in addition to and/or in association with detecting false FHR value errors, the signal processing component 202 can perform additional processing of the doppler ultrasound signal that facilitates improving the overall performance of the FMS 100 and process 400. This additional processing is rooted in determining and analyzing the SNR of the signal. To facilitate this end, the signal processing component 202 can include SNR assessment component 216, artifact assessment component 218, cross-talk assessment component 220, adaptive averaging component 222 and repositioning component 224.

As previously mentioned, the doppler ultrasound signal can be affected by various sources of noise, including electrical interference, maternal movements, and other artifacts. The SNR value of the doppler ultrasound signal represents the amount/intensity of noise in the signal relative to the amount/intensity of signals of interest over a given time frame evaluated (e.g., peaks/signals corresponding to heartbeats of the targeted fetal heart). To this end, the SNR of the doppler signal reflects the quality of the doppler signal, wherein the higher the SNR, the better the quality. In various embodiments, the SNR assessment component 216 can employ one or more SNR estimation functions to determine SNR values of the doppler signal data in real-time in association with performing the FHR estimation and error detection processes described herein. For example, the SNR assessment component 216 can repeatedly compute SNR values for respective consecutive portions of the doppler signal data corresponding to any time period, such as every one minute, less than one minute, or greater than one minute. The signal processing component 202 can further employ the SNR values as a process variable in association with detecting false first FHR values and/or performing various additional functions that improve the overall performance of the fetal monitoring session, as described with reference to FIG. 7.

Figure 7:
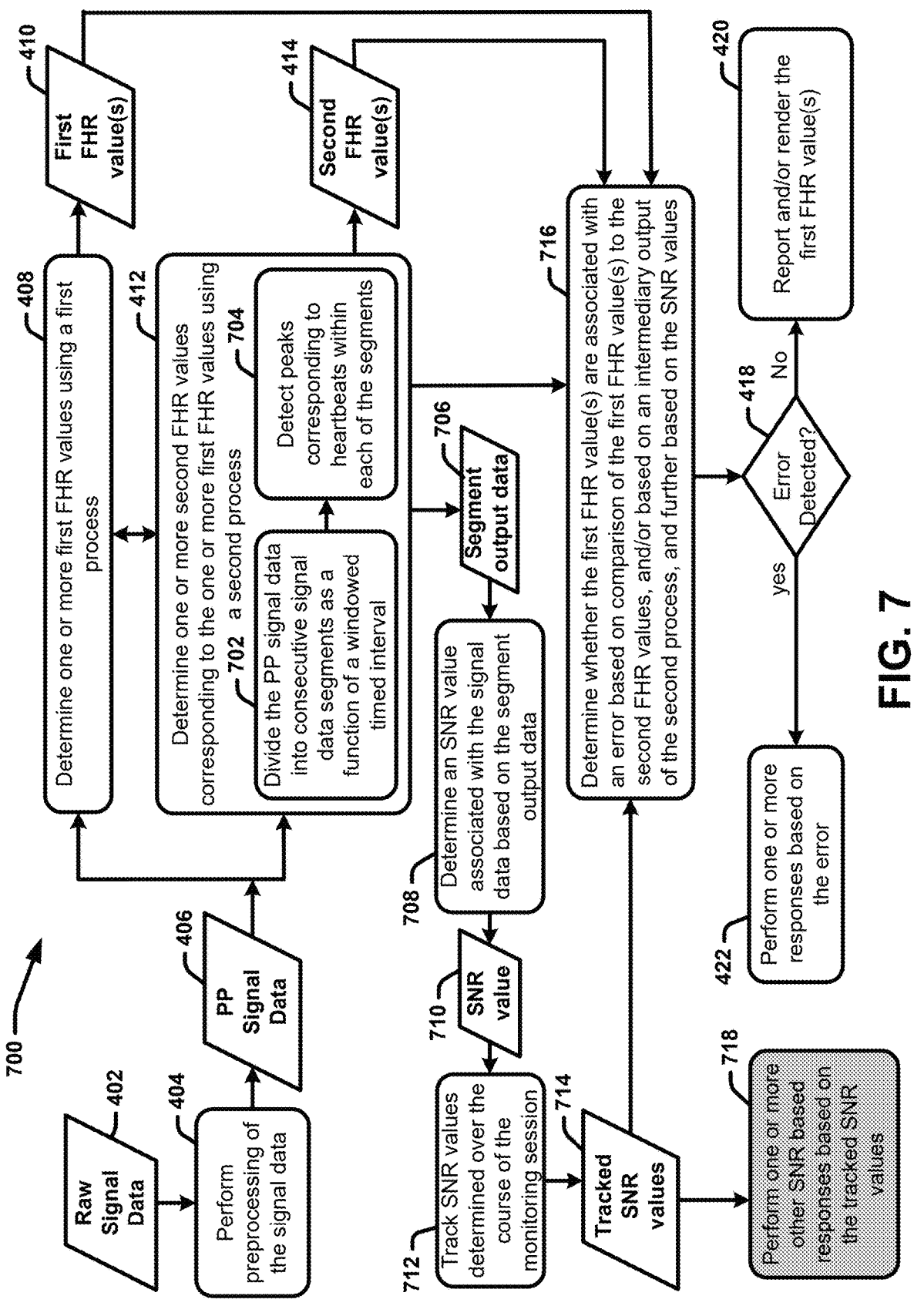
FIG. 7 presents a flow diagram of another example real-time doppler ultrasound signal processing process for fetal heartbeat detection with supervisory error control, in accordance with one or more embodiments of the disclosed subject matter.

FIG. 7 presents a flow diagram of another example real-time doppler ultrasound signal processing process 700 for fetal heartbeat detection with supervisory error control, in accordance with one or more embodiments of the disclosed subject matter. Process 700 corresponds to process 400 with the addition of SNR based features. Corresponding aspects of process 700 previously described with reference to process 400 (e.g., elements enumerated 402-426) are omitted for sake of brevity.

With reference to FIG. 7 in view of FIGS. 1-6C, in accordance with process 700, the second process performed at 412 corresponds to the windowing process described with reference to process 400. The windowing process can correspond to the fixed windowing process or the adaptive windowing process. To this end, at 702, the windowing component 208 divides the PP signal data 406 into consecutive signal data segments as a function of a windowed time interval as the PP signal data 406 is received. For example, as applied to fixed windowing, the windowing component 208 can apply the same fixed duration for the windowed time interval. Alternatively, as applied to adaptive windowing, the windowing component 208 can adapt the duration for the windowed time interval for each segment (e.g., as shown in FIG. 6B), or adapt the duration of the windowed time interval at lower rate (e.g., as function of time and/or number of consecutive segments) such that a plurality of consecutive segments corresponding to a particular time period (e.g., one minute or another defined or variable time period) have the same window size/duration.

At 704, the supervisory FHR estimation component 210 separately evaluates, each of the signal data segments in association with detecting one or more peaks included in the respective segments corresponding to heartbeats as the respective segments are generated. To this end, as applied to fixed windowing, for each segment of the consecutive signal data segments, using one or more peak detection algorithms, the supervisory FHR estimation component 210 can detect one or more signal peak included in the segment respectively corresponding a heartbeat of the fetal heart or determine that the segment does not include any signal peaks corresponding to a heartbeat. On the other hand, as applied to adaptive windowing, for each segment of the consecutive signal data segments, using one or more peak detection algorithms, the supervisory FHR estimation component 210 can detect only a single signal peak included in the segment corresponding a heartbeat or determine that the segment excludes a signal peak corresponding to the heartbeat. Additionally, or alternatively, as applied to pattern recognition, for each segment of the consecutive signal data segments, using the pattern assessment component 212, the supervisory FHR estimation component 210 can detect whether the segment includes one or more fetal heartbeats (or not) based on matching the signal pattern to a corresponding representation that corresponds to one or more fetal heartbeats.

Regardless as to whether fixed windowing, adaptive windowing and/or pattern recognition is used, as described with reference to process 400, at 412 the supervisory FHR estimation component 210 further aggregates and tracks the number of fetal heartbeats detected for respective signal data segments included in a portion of the PP signal data 406 corresponding to a defined timeframe, such as one minute or another defined timeframe. This portion of the PP signal data 406 corresponds to the same portion being processed in parallel at 408 via the first process in association with determining the one or more first FHR values 410. The supervisory FHR estimation component 210 further determines one or more second FHR values 414 (corresponding to the one or more first FHR values 410) based on the number of fetal heartbeats detected over the defined period of time (e.g., such as a single second FHR value as applied to the period of time being one minute and the FHR value being in BPM).

To this end, the output of the second process performed at 412 can include the one or more second FHR values 414 as well as segment output data 706. The segment output data 706 corresponds to the respective consecutive signal data segments generated at 702 along with information identifying the single peak (or lack thereof) included in the respective segments corresponding to the fetal heartbeat. The segment output data 706 can reflect provision of the respective signal data segments and their corresponding peak information to the SNR assessment component 216 as they are respectively generated in real-time (e.g., as opposed to aggregating all the segments for the portion after the corresponding timeframe has occurred, such as all the segments making up the last one minute or the like). Alternatively, the segment output data 706 can reflect provision of the respective signal data segments and their corresponding peak information to the SNR assessment component 216 as aggregated for the portion after the corresponding timeframe has occurred, such as all the segments making up the last one minute or the like.

At 708, the SNR assessment component 216 determines an SNR value 710 associated with the signal data (e.g., the PP signal data 406 and thus the raw signal data 402 from which it was generated) based on the segment output data 706. In particular, at 708 the SNR assessment component 216 can determine an SNR value for a portion of the signal data based on a set of segments corresponding to the portion, such as the same current portion for which the current first and second FHR values are based, and/or another portion corresponding to another timeframe. To this end, in association with determining the SNR value 710, the SNR assessment component 216 can separately evaluate each segment in the set and aggregate the result of all segments in the set to calculate the SNR value 710.

In this regard, in one or more embodiments, for each segment, the SNR assessment component 216 determines a threshold between signal peak value for the segment based on a highest signal peak value associated with the segment relative to other signal peak values associated with the segment. For example, the SNR function used by the SNR assessment component 216 can employ an adaptive threshold, such as X percent (e.g., 25 percent, 20 percent, or another percentage threshold) of the highest signal peak amplitude value within a signal data segment. In this manner, the threshold signal peak value determined for each of the separate signal data segments is tailored to each segment and can vary for different segments. In other words, as the highest signal peak value can vary from segment to segment, the resulting peak threshold can vary from segment to segment. For the given segment, the SNR assessment function further counts the signal peaks crossing the peak threshold as signals of interest and signal peaks within the peak threshold as noise. In some implementations, the SNR assessment component 216 can determine an SNR value for the given segment based on the number of peaks corresponding to noise and the number of peaks corresponding to signals of interest (and optionally their respective amplitudes). With these embodiments, the SNR value 710 can correspond to an average of the individual SNR values determined for each segment in the set. In other embodiments, the SNR assessment component can aggregate the number of peaks corresponding to noise (and optionally their respective amplitudes) and the aggregate number of peaks corresponding to signals of interest (and optionally their respective amplitudes) across all the segments of a given set and thereafter calculate the SNR value 710 based thereon. In either of these embodiments, the SNR value 710 reflects the aggregate number of peaks corresponding to noise (and optionally their respective amplitudes) and the aggregate number of peaks corresponding to signals of interest (and optionally their respective amplitudes) across all the segments of a given set and thereafter calculate the SNR value 710 based thereon.

In some embodiments, the SNR calculation performed at 708 can also use the output of the peak detection algorithm employed at 704 with respect to each of the signal data segments to understand which peaks are artifacts and count these peaks as noise despite being above the peak threshold. With these embodiments, in association with processing each segment at 708, the artifact assessment component 218 can employ the one or more signal peaks detected for the segment to identify any signal peaks other than the one or more signal peaks exceeding the threshold peak value determined for that segment. The artifact assessment component 218 can further classify these peaks as artifacts and the SNR assessment component 216 can exclude peaks corresponding to artifacts in association with calculating the SNR value 710, and/or value peaks corresponding to artifacts as noise in association with calculating the SNR value at 710 (which otherwise would have been considered as valid signals of interest). In other words, artifact assessment component 218 can identify artifact signal peaks associated with the consecutive signal data segments corresponding to artifacts and the SNR assessment component can exclude the artifact signal peaks in association with determining the SNR values.

In some embodiments, motion data generated in real-time via an accelerometer or another suitable motion sensor of the FSD 104 can also be used by the artifact assessment component 218 to facilitate identifying signals corresponding to artifacts as a result of motion or movement by the mother. With these embodiments, the artifact assessment component 218 can correlate the motion data to corresponding peaks included in respective portions of the signal data evaluated at 710 and classify these peaks as artifacts (e.g., in real-time and based on timing of occurrence), wherein based on classification of a signal peak as an artifact peak, the SNR assessment component 216 can exclude the artifact peak from the SNR calculation.

In other embodiments, the SNR assessment component 216 can employ alternative techniques to generate SNR values for the PP signal data 406. The SNR values produced by this method and without this method will help generate metrics related to the amount of artifact in the signal that can be used to warn the clinician or actively compensate for the same. For example, in some embodiments, in addition to excluding artifact peaks from the SNR calculation and/or counting artifacts peaks as noise in the SNR calculation, the artifact assessment component 216 can further track artifact information regarding the frequency and amount (e.g., number and amplitude) of artifacts detected in the signal data over time, as updated in real-time. The artifact assessment component 218 can further report the artifact information to the monitor device and/or the monitor device 102 can render the artifact information during the course of the monitoring session. In other embodiments, the artifact assessment component 218 can generate warning or notification information (e.g., that can be reported/rendered in real-time) in response to the amount and/or frequency of the detected artifacts corresponding to a warning condition.

Continuing with process 700, at 712, the SNR assessment can further track and aggregate SNR values (e.g., tracked SNR values 714) determined for respective consecutive portions of the signal data over time (e.g., over the course of the fetal monitoring session). To this end, it should be appreciated that process 700 corresponds to a continuous process and thus at 708, the SNR assessment component 216 can repeatedly determine an updated SNR value 710 for respective new portions of the signal data as they are processed at 412. Thus, the SNR values 714 can include one or more current SNR values respectively determined based on respective current portions of the signal data corresponding to the current portions for which the one or more current first and second FHR values are based, as well as previously determined SNR values. In this manner, trends or patterns in the SNR values 714 over the course of the fetal monitoring session can be used to assess various conditions associated with the fetal monitoring session (in association with performing one or more other SNR based responses based on the tracked SNR values at 716, as discussed below).

In some embodiments, continuing with process 700, at 716, the error detection component 214 can determine whether the one or more first FHR values 410 are associated with an error based on comparison of the one more first FHR values 410 to the corresponding one or more second FHR values 414 and/or based on an intermediary output of the second process (as described with reference to process 400), and further based on the SNR values (e.g., the tracked SNR values 714 and/or a subset of the SNR values 714 corresponding to the portion or portions of the PP signal data 406 for which the current first and second FHR values are based). For example, in some embodiments, one or more of the preprocessing functions used to generate the PP signal data 406, such one or more digital adaptive gain control functions, can tend to amplify even small signals (only noise signals) with no actual doppler shifted information in it from a fetal heart. This results in the production of some spurious or false heart rates using autocorrelation processing and typically occurs when the SNR associated with the portion of the signal data for which the false first FHR value is based is low (e.g., relative to a defined threshold). Thus, in accordance with this example, the error detection component 214 can identify such spurious first FHR values based on being correlated to one or more low SNR values (e.g., relative to one or more thresholds) and classify them as false values at 716.

As noted above, trends or patterns in the SNR values 714 over the course of the fetal monitoring session can also be used to assess various conditions associated with the fetal monitoring session in association with performing one or more other SNR based responses based on the tracked SNR values at 716. To this end, in some embodiments, at 716 process 700 can include performing one or more other responses (e.g., other than the accuracy based assessment discussed below) based on the tracked SNR values 714, which can include generating (e.g., via artifact assessment component 218) artifact information in real-time identifying peaks corresponding to artifacts and facilitating rendering (e.g., via reporting component 226 and/or rendering component 302) the artifact information in real-time (e.g., via one or more visual indicators applied to the CTG tracing data or the like). In some embodiments, the artifact assessment component 218 can further track the amount of artifacts observed in the signal data (e.g., the PP signal data 406 which corresponds to the raw signal data 402) to gauge the amount of artifacts observed in the signal data over time and/or generation artifact information regarding the same for rendering and/or controlling other system responses (e.g., generating alarms/notifications, recommending repositioning of the FSD or the like).

Additionally, or alternatively, the tracked SNR values 714 can be used to control (e.g., stop or reduce) the influence of the second process performed at 412 on the final rendered FHR values based on the SNR of the signal. For example, in some embodiments, at 716, the error detection component 214 can assess the accuracy of the one or more second FHR values 414 based on the one or more corresponding SNR values and/or another subset of the tracked SNR values 714 over a recent period of time up to the current point in time. In some embodiments, the error detection component 214 can determine whether the accuracy is acceptable or not based on the one or more SNR values being above (and thus an acceptable level of accuracy) or below (and thus an unacceptable level of accuracy) one or more defined SNR value thresholds. With these embodiments, based on a determination that the accuracy is not acceptable, the error detection component 214 can assume the one or more second FHR values are likely to be inaccurate, and thus default to relying on the one or more first FHR values 410. In other words, the based on a determination that the accuracy is not acceptable, at 418 the error detection component 214 can classify the one or more first FHR values as being accurate (e.g., not associated with an error) regardless of whether they deviate from the corresponding second FHR values 414. The signal processing component 202 can also temporarily deactivate calculation of the second FHR values in accordance with the second process (e.g., and thus saving computational resources and power) while the SNR remains low and reactivate the same when the SNR increases above the threshold. In this manner, the signal processing component 202 can regulate usage of the second process for error detection based on the tracked SNR values of the doppler signal.

In other embodiments, at 716 the error detection component 214 can weigh the difference between a first FHR value and a corresponding second FHR value based on the corresponding SNR value associated with the portion of the signal data for which the respective first and second FHR values are based in association with determining whether the first FHR value is false and/or corresponds to a DC or HC error.

Additionally, or alternatively, the one or more other SNR based responses performed at 718 can include identifying and responding to incidences of crosstalk, referred to herein as crosstalk conditions. Crosstalk refers to the interference or overlap of signals between ultrasound transducers of different FSDs 104 in implementations in which two or more FDSs 104 are used to simultaneously monitoring a corresponding number of fetuses of the same mother (e.g., as applied to twins, triplets, and so one), or more specifically, one FSD picking up the signals of another FSD, primarily due to frequency aliasing effects in the demodulation process. With these embodiments, the crosstalk assessment component 220 can identify a crosstalk condition by looking for specific behavior in SNR of the signal as the harmonics would be repetitive and at higher frequencies than expected. For example, the crosstalk assessment component 220 can evaluate the tracked SNR values 714 associated with a current portion (or another portion) and determine whether the corresponding portion of the signal data includes noise attributed to crosstalk based on the corresponding SNR values exhibiting a pattern corresponding to a crosstalk condition, such as a sinusoidal pattern. With these embodiments, one or more previously classified SNR patterns corresponding to crosstalk conditions (e.g., as stored in memory 230 or the like) can be employed by the crosstalk assessment component 220. The FMS system can further respond to detected incidences of crosstalk accordingly. For example, in some implementations, based on reported incidences of crosstalk (e.g., reported in real-time via reporting component 226 in response to identification thereof via the crosstalk assessment component 220), the rendering component 302 can generate and render corresponding notifications and/or preventative warnings. Additionally, alternatively, false fetal parameters (e.g., FHR values, fetal movement values, etc.) being rendered as an effect can be identified via the crosstalk assessment component 220 and flagged or eliminated. In this regard, in some embodiments, the error assessment performed at 716 can also involve correlating a detected crosstalk condition to one or more first FHR values and classifying the one or more first FHR values as false values based on being associated with the crosstalk condition.

The one or more other SNR based responses performed at 718 can also include regulating an amount of averaging of the final rendered FHR values (e.g., either the first FHR values and/or the second FHR values) using SNR of the process variable. Averaging of the FHR output refers to averaging two or more consecutive FHR values measured over time. In various embodiments, the signal processing component 202 (and/or the master signal processing component 306) can perform averaging of the FHR output rendered via the monitor device 102 (or another device), and selectively decrease (e.g., to a degree of no averaging) and increase the amount of averaging of the rendered FHR output based on the SNR of the doppler signal. For example, if the SNR of the doppler signal is high (e.g., relative to a defined threshold or range), then the FMS can measure and render the FHR based on real-time beat to beat time differences, and not perform any averaging of consecutive FHR values. On the other hand, if the SNR is low (e.g., relative to one or more defined thresholds or threshold ranges), then the FMS can average two or more consecutive FHR values. In some implementations, the FMS can tailor the amount of the averaging with respect to the number of consecutive FHR values averaged, based on the SNR such that as the SNR decreases, the number of consecutive FHR values averaged increases. By removing the averaging when the SNR of the signal is high (e.g., relative to one or more thresholds), the FMS can generate and/or facilitate a more accurate, real-time interpretation of the FHR, resulting in better clinical outcomes.

Thus, in some embodiments, the adaptive averaging component 222 can monitor the SNR of the doppler signal (e.g., the tracked SNR values 714) and determine whether and to what degree the signal processing component 202 and/or the master signal processing component 306) should average the rendered FHR output based on the SNR and defined criteria correlating different SNR values or value ranges to different amounts of averaging (including no averaging). For instance, the defined criteria may indicate no averaging is to be performed if the SNR exceeds an upper threshold, averaging of two consecutive FHR values is to be performed if the SNR is within a median range, and averaging of four consecutive FHR values it to be performed if the SNR is less than a minimum threshold. The adaptative averaging component 222 can further instruct the signal processing component 202 and/or the master signal processing component 306 to apply the appropriate amount of adaptive averaging or no adaptive averaging, accordingly.

The one or more other SNR based responses performed at 718 can also include generating (e.g., via SNR assessment component 216) and rendering (e.g., via rendering component 302) signal quality information representing the quality of the doppler signal in real-time based on the current SNR value (e.g., SNR value 710) and the tracked SNR values 714. For example, in some embodiments, the signal quality information can include the current SNR value and/or an average of the most recent SNR values. In other embodiments, the signal quality information can reflect another measure of signal quality determined as a function of the current SNR value and/or the most recent group of SNR values (e.g., a score, a bar, a percentage or another valuation of signal quality), wherein the measure increases as the SNR increases (e.g., higher SNRs means better signal quality relative to lower SNRs) and decreases as the SNR increases. For example, based on the current SNR values, the signal SNR assessment component 216 can generate and report a dynamic signal quality measure in real-time representative of the current level of quality of the signal data, such as a signal quality score on a suitable scale (e.g., such as 1 out of 10, with 10 corresponding to the strongest or highest signal quality and 1 corresponding to the weakest or lowest) or another measure of signal quality (e.g., strong, medium, weak, or the like).

The one or more other SNR responses performed at 718 can also include generating (e.g., via repositioning assessment component 224) and rendering (e.g., via rendering component 302) an early repositioning indication recommending repositioning of the FSD 104 on the mother based on trends or patterns in the tracked SNR values. With these embodiments, the repositioning assessment component 224 can determine that the FSD 104 may need to be repositioned based on observing a steady decline in the SNR values, (which would indicate the fetus's movement away from the beam of the ultrasound transducer 238) and generate/report a repositioning warning to the monitor device 102 for rendering in real-time. In other words, the repositioning assessment component 224 can monitor the SNR values during the fetal monitoring session and generate a repositioning indication recommending repositioning of the ultrasound transducer (e.g., or more generally the FSD 104 comprising the ultrasound transducer 238) based on detecting a decline in the SNR values in association with the monitoring.

In some embodiments, the SNR values determined and reported in real-time, or the corresponding signal quality measure determined and reported in real-time, can also be used as an aid in the repositioning of the FSD 104. For example, in association with repositioning the FSD 104, the medical professional (or another suitable entity) moving the FSD 104 about the mother can monitor the SNR values and/or the signal quality measure, wherein an increase to the SNR values and/or the signal quality measure indicates movement of the FSD 104 in closer alignment with the targeted fetal heart and wherein a decrease to the SNR values and/or the signal quality measure indicates movement of the FSD 104 farther away from the optimal alignment with the targeted fetal heart. In some implementations of these embodiments, the repositioning assessment component 224 can monitor the SNR values and/or the signal quality measure (in addition to or opposed to the medical professional performing the movement) and generate and report repositioning guide information in real-time indicating whether the current position is satisfactory or not based on whether the SNR values and/or the signal quality measure satisfies defined satisfactory criteria (e.g., an acceptable SNR level and/or an acceptable signal quality measure value). For example, the repositioning guide information may merely instruct the medical professional to keep adjusting the position of the FSD 104 so long as the satisfactory criteria have not been meet, and in response to a determination that the satisfactory criteria has been met, the repositing guide information can inform the medical professional that the current position of the FSD 104 is satisfactory and to stop moving the FSD 104 and keep the FSD 104 at the current position.

Figure 8:
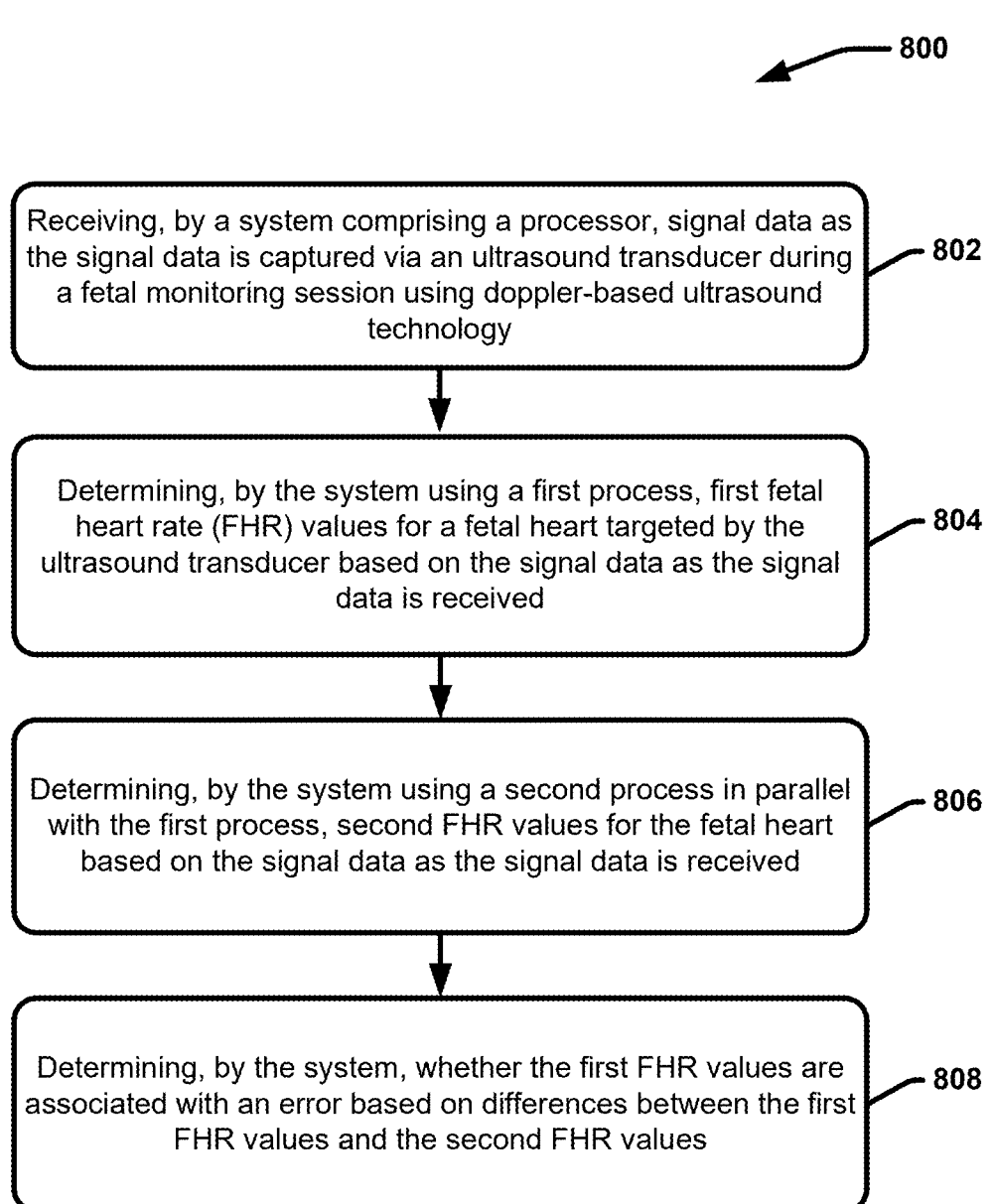
FIG. 8 illustrates a block diagram of an example, non-limiting computer implemented method that facilitates real-time doppler ultrasound signal processing for fetal heartbeat detection with supervisory error control, in accordance with one or more embodiments of the disclosed subject matter.

FIG. 8 illustrates a block diagram of an example, non-limiting computer implemented method 800 that facilitates real-time doppler ultrasound signal processing for fetal heartbeat detection with supervisory error control, in accordance with one or more embodiments of the disclosed subject matter. Method 800 comprises at 802, receiving, by a system comprising a processor (e.g., FMS system 100, FSD 104 and/or monitor device 102), signal data as the signal data is captured via an ultrasound transducer during a fetal monitoring session using doppler-based ultrasound technology. At 804, method 800 comprises determining, by the system using a first process (e.g., an autocorrelation process or another process excluding the second process), first fetal heart rate (FHR) values (e.g., first FHR values 410, via primary FHR estimation component 206) for a fetal heart targeted by the ultrasound transducer based on the signal data as the signal data is received. At 806, method 800 comprise determining, by the system using a second process in parallel with the first process, second FHR values for the fetal heart based on the signal data as the signal data is received (e.g., via windowing component 208 and supervisory FHR estimation component 210). At 808, method 800 comprises determining, by the system, whether the first FHR values are associated with an error based on differences between the first FHR values and the second FHR values (e.g., via error detection component 214).

FIG. 9 illustrates a block diagram of an example, non-limiting computer implemented method 900 that facilitates real-time doppler ultrasound signal processing for fetal heartbeat detection with supervisory error control, in accordance with one or more embodiments of the disclosed subject matter. Method 900 comprises at 902, receiving, by a system comprising a processor (e.g., FMS system 100, FSD 104 and/or monitor device 102), signal data as the signal data is captured via an ultrasound transducer during a fetal monitoring session using doppler-based ultrasound technology. At 904, method 900 comprises dividing, by the system, the signal data into consecutive signal data segments as a function of one (e.g., a fixed duration) or more (e.g., an adaptive duration) windowed time intervals as the signal data is received (e.g., via windowing component 208). At 906, method 900 comprises performing, by the system, separate signal-to-noise ratio (SNR) assessments tailored to each segment of the consecutive signal data segments as they are generated (e.g., via SNR assessment component 216). At 908, method 900 comprises determining, by the system, SNR values associated with the signal data based on aggregated results of the separate SNR assessments (e.g., via SNR assessment component 216). At 910, method 900 comprises generating, by the system, signal quality information indicating a measure of quality of the signal data as the signal data is received based on the SNR values (e.g., via SNR assessment component 216).

In various embodiments, method 900 can further comprise rendering, by the system, the signal quality information via an electronic output device as the signal quality information is generated. Additionally, or alternatively, method 900 can further comprise monitoring, by the system, the SNR values during the fetal monitoring session, generating, by the system, a repositioning indication recommending repositioning of the ultrasound transducer based on detecting a decline in the SNR values in association with the monitoring.

Additionally, or alternatively, method 900 can further comprise identifying, by the system, a crosstalk condition associated with the signal data as the signal data is received based on a pattern reflected in the SNR values corresponding to the crosstalk condition, and generating, by the system, a crosstalk notification identifying the crosstalk condition. In some implementations of these embodiments, method 900 can also comprise generating, by the system, measures of one or more fetal parameters based on the signal data, the one or more fetal parameters comprising a heart rate of a fetus monitored via the fetal monitoring session or movement of the fetus, identifying, by the system, one or more of the measures associated with the crosstalk condition, and preventing, by the system, rendering of the one or more measures via an electronic output device during the fetal monitoring session.

Additionally, or alternatively, method 900 can further comprise generating, by the system based on the signal data, heart rate values of a heart of a fetus being monitored via the fetal monitoring session, and regulating, by the system, an amount of averaging of the fetal heart rate values in association with the generating based on the SNR values.

Additionally, or alternatively, method 900 can further comprise determining, by the system, artifact information regarding artifacts reflected in the signal data based on the SNR values, and rendering, by the system, the artifact information via an electronic output device.

Additionally, or alternatively, method 900 can further comprise generating, by the system, measures of one or more fetal parameters based on the signal data, the one or more fetal parameters comprising a heart rate of a fetus monitored via the fetal monitoring session or movement of the fetus, identifying, by the system, one or more of the measures associated with an error based on the SNR values, and preventing, by the system, rendering of the one or more measures via an electronic output device during the fetal monitoring session.

Additionally, or alternatively, in accordance with method 900, the determining the SNR values can comprise distinguishing, by the system, between signals of interest and noise signals based on a threshold signal peak value determined for each of the consecutive signal data segments that varies based on respective highest signal peak values associated with each of the consecutive signal data segments. The determining the SNR values can further comprise identifying, by the system, signal peaks corresponding to artifacts despite corresponding signal peak values for the signals peaks exceeding the threshold signal peak value, and excluding, by the system, the signal peaks corresponding to the artifacts in association with calculating the SNR values, or valuing, by the system, the signal peaks corresponding to the artifacts as noise in association with calculating the SNR values.

FIG. 10 illustrates a block diagram of another example, non-limiting computer implemented method 1000 that facilitates real-time doppler ultrasound signal processing for fetal heartbeat detection with supervisory error control, in accordance with one or more embodiments of the disclosed subject matter. Method 1000 comprises, at 1002 receiving, by a system comprising a processor (e.g., FMS system 100, FSD 104 and/or monitor device 102), signal data as the signal data is captured via an ultrasound transducer during a fetal monitoring session using doppler-based ultrasound technology. At 1004, method 1000 comprises determining, by the system, fetal heart rate (FHR) values for a fetal heart targeted by the ultrasound transducer based on the signal data as the signal data is received. At 1006, method 1000 comprises determining, by the system, SNR values associated with the signal data as the signal data is received in accordance with a windowing process. At 1008, method 1000 comprises determining, by the system, whether the FHR values are associated with one or more issues based on the SNR values, the one or more issues selected from the group consisting of, an error value (e.g., a spurious value, a half count error value or a double count error value), an artifact issue, a signal quality issue, a crosstalk issue, and a repositioning issue. At 1010, method 1000 comprises rendering, by the system, a notification via a monitor device based on determining occurrence of an issue.

Example Operating Environments

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. To this end, a computer readable storage medium, a machine-readable storage medium, or the like as used herein can include a non-transitory computer readable storage medium, a non-transitory machine-readable storage medium, and the like.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 11, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 11:
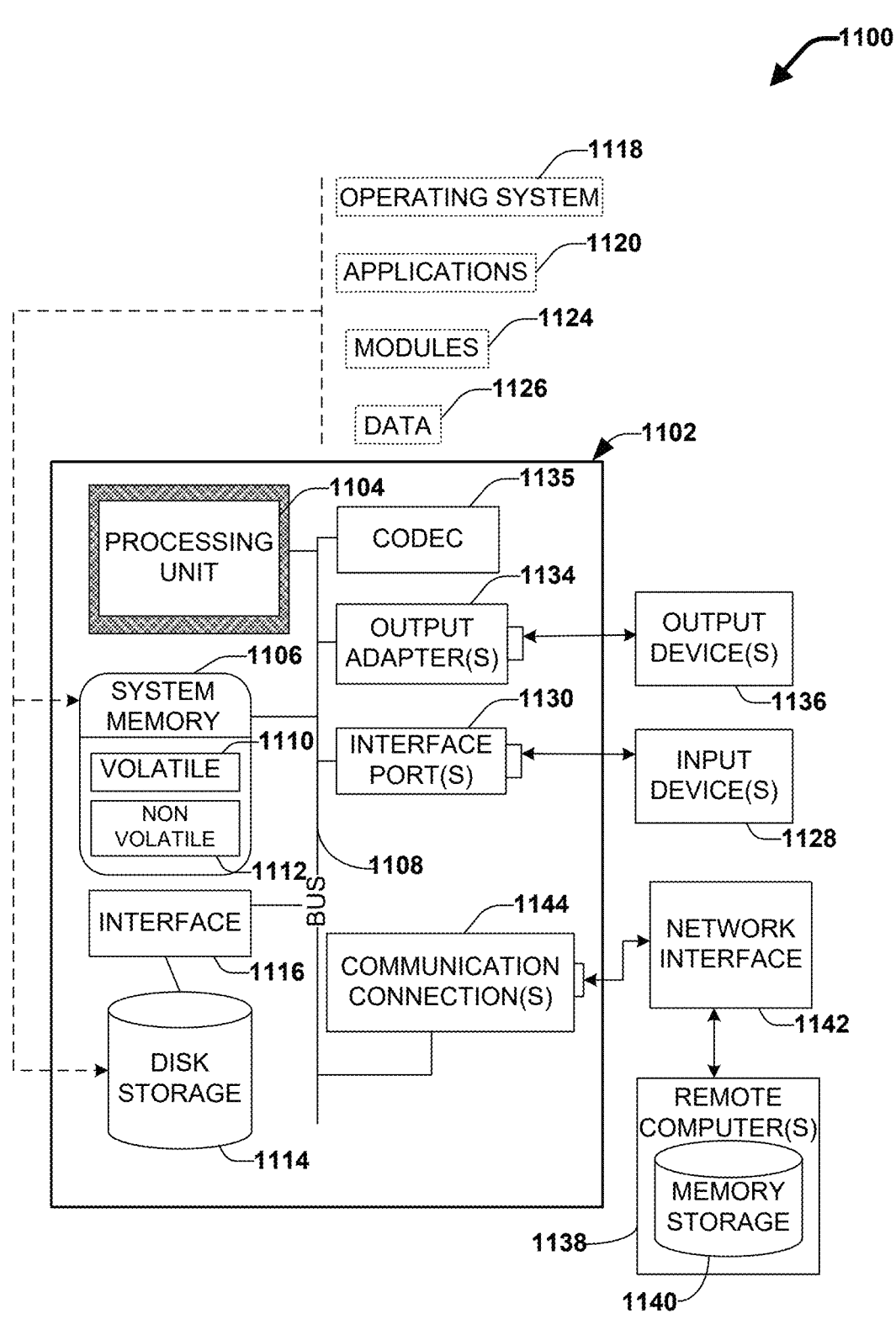
FIG. 11 illustrates a block diagram of an example, non-limiting operating environment in which one or more embodiments described herein can be facilitated.

With reference to FIG. 11, an example environment 1100 for implementing various aspects of the claimed subject matter includes a computer 1102. The computer 1102 includes a processing unit 1104, a system memory 1106, a codec 1135, and a system bus 1108. The system bus 1108 couples system components including, but not limited to, the system memory 1106 to the processing unit 1104. The processing unit 1104 can be any of various available processors. Dual microprocessors and other multiprocessor architectures also can be employed as the processing unit 1104.

The system bus 1108 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13114), and Small Computer Systems Interface (SCSI).

The system memory 1106 includes volatile memory 1110 and non-volatile memory 1112, which can employ one or more of the disclosed memory architectures, in various embodiments. The basic input/output system (BIOS), containing the basic routines to transfer information between elements within the computer 1102, such as during start-up, is stored in non-volatile memory 1112. In addition, according to present innovations, codec 1135 can include at least one of an encoder or decoder, wherein the at least one of an encoder or decoder can consist of hardware, software, or a combination of hardware and software. Although, codec 1135 is depicted as a separate component, codec 1135 can be contained within non-volatile memory 1112. By way of illustration, and not limitation, non-volatile memory 1112 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1112 can employ one or more of the disclosed memory devices, in at least some embodiments. Moreover, non-volatile memory 1112 can be computer memory (e.g., physically integrated with computer 1102 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1110 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1102 can also include removable/non-removable, volatile/non-volatile computer storage medium. FIG. 11 illustrates, for example, disk storage 1114. Disk storage 1114 includes, but is not limited to, devices like a magnetic disk drive, solid state disk (SSD), flash memory card, or memory stick. In addition, disk storage 1114 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1114 to the system bus 1108, a removable or non-removable interface is typically used, such as interface 1116. It is appreciated that disk storage 1114 can store information related to a user. Such information might be stored at or provided to a server or to an application running on a user device. In one embodiment, the user can be notified (e.g., by way of output device(s) 1136) of the types of information that are stored to disk storage 1114 or transmitted to the server or application. The user can be provided the opportunity to opt-in or opt-out of having such information collected or shared with the server or application (e.g., by way of input from input device(s) 1128).

It is to be appreciated that FIG. 11 describes software that acts as an intermediary between users and the basic computer resources described in the suitable operating environment 1100. Such software includes an operating system 1110. Operating system 1110, which can be stored on disk storage 1114, acts to control and allocate resources of the computer 1102. Applications 1120 take advantage of the management of resources by operating system 1110 through program modules 1124, and program data 1126, such as the boot/shutdown transaction table and the like, stored either in system memory 1106 or on disk storage 1114. It is to be appreciated that the claimed subject matter can be implemented with various operating systems or combinations of operating systems.

A user enters commands or information into the computer 1102 through input device(s) 1128. Input devices 1128 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1104 through the system bus 1108 via interface port(s) 1130. Interface port(s) 1130 include, for example, a serial port, a parallel port, a game port, and a universal serial bus (USB). Output device(s) 1136 use some of the same type of ports as input device(s) 1128. Thus, for example, a USB port can be used to provide input to computer 1102 and to output information from computer 1102 to an output device 1136. Output adapter 1134 is provided to illustrate that there are some output devices 1136 like monitors, speakers, and printers, among other output devices 1136, which require special adapters. The output adapters 1134 include, by way of illustration and not limitation, video and sound cards that provide a means of connection between the output device 1136 and the system bus 1108. It should be noted that other devices or systems of devices provide both input and output capabilities such as remote computer(s) 1138.

Computer 1102 can operate in a networked environment using logical connections to one or more remote computers, such as remote computer(s) 1138. The remote computer(s) 1138 can be a personal computer, a server, a router, a network PC, a workstation, a microprocessor based appliance, a peer device, a smart phone, a tablet, or other network node, and typically includes many of the elements described relative to computer 1102. For purposes of brevity, only a memory storage device 1140 is illustrated with remote computer(s) 1138. Remote computer(s) 1138 is logically connected to computer 1102 through a network interface 1142 and then connected via communication connection(s) 1144. Network interface 1142 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1144 refers to the hardware/software employed to connect the network interface 1142 to the bus 1108. While communication connection 1144 is shown for illustrative clarity inside computer 1102, it can also be external to computer 1102. The hardware/software necessary for connection to the network interface 1142 includes, for exemplary purposes only, internal and external technologies such as, modems including regular telephone grade modems, cable modems and DSL modems, ISDN adapters, and wired and wireless Ethernet cards, hubs, and routers.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SL-DRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A method, comprising:
receiving, by a system comprising a processor, signal data as the signal data is captured via an ultrasound transducer during a fetal monitoring session using doppler-based ultrasound technology;
determining, by the system using a first process, first fetal heart rate (FHR) values for a fetal heart targeted by the ultrasound transducer based on the signal data as the signal data is received;
determining, by the system using a second process in parallel with the first process, second FHR values for the fetal heart based on the signal data as the signal data is received; and determining, by the system, whether the first FHR values are associated with an error based on differences between the first FHR values and the second FHR values, wherein the error comprises at least one of a double-count error, a half-count error, or a false value, and wherein upon detecting the error the system substitutes error-free second FHR values and controls generation of an alarm or output rendering accordingly, and wherein the system dynamically adjusts an amount of averaging applied to at least one of the first and second FHR values as a function of signal-to-noise ratio values computed from segmented Doppler ultrasound signal data.

2. The method of claim 1, wherein the error comprises one or more of the FHR values corresponding to a false value.

3. The method of claim 1, wherein the error comprises at least one of, a double-count error or a half-count error.

4. The method of claim 1, further comprising, based on a determination that one or more of the first FHR values are associated with the error:
generating, by the system, error information identifying the error; and
rendering, by the system, the error information via an electronic output device in association with rendering FHR information indicating the first FHR values; or
facilitating rendering, by the system, one or more of the second FHR values corresponding to the one or more first FHR values via the electronic output device as opposed to facilitating rendering, by the system, the one or more of the first FHR values.

5. The method of claim 1, further comprising, based on a determination that one or more of the first FHR values are associated with the error:
controlling, by the system, generation of an alarm by the system or an external system regarding the one or more of the first FHR values satisfying an alarm criterion.

6. The method of claim 1, wherein the second process comprises:
dividing, by the system, the signal data into consecutive signal data segments as a function of a windowed time interval as the signal data is received; and
separately evaluating, by the system, each segment of the consecutive signal data segments as they are generated in association with detecting signal peaks corresponding to heartbeats of the fetal heart.

7. The method of claim 6, wherein the second process comprises employing a fixed duration for the windowed time interval during the fetal monitoring session.

8. The method of claim 6, wherein the second process comprises adapting a duration of the windowed time interval during the fetal monitoring session based on one or more parameters determined using the first process.

9. The method of claim 6, wherein the separately evaluating comprises, for each segment of the consecutive signal data segments:
identifying, by the system, one or more signal peaks included in the segment respectively corresponding to a heartbeat of the fetal heart; or
determining, by the system, that the segment excludes any signal peaks corresponding to heartbeats.

10. The method of claim 9, further comprising:
determining, by the system, one or more signal-to-noise ratio (SNR) values associated with the signal data based on the consecutive signal data segments, comprising for each segment of the consecutive signal data segments:

distinguishing, by the system, between signals of interest and noise signals based on a threshold signal peak value determined for the segment based on a highest signal peak value associated with segment relative to other signal peak values associated with the segment;

employing, by the system, the one or more signal peaks to identify artifact signals exceeding the threshold signal peak value other than the one or more signal peaks; and excluding, by the system, any identified artifact signals in association with determining the one or more SNR values.

11. The method of claim 1, further comprising:

identifying, by the system, distinct patterns observed in the signal data over a first period of the time; and classifying, by the system, the distinct patterns into corresponding fetal heartbeat representations, and wherein the second process comprises:

determining, by the system, the second FHR values based on identifying one or more of the distinct patterns in the signal data over a second period after the first period of time.

12. A fetal monitoring system (FMS), comprising:

at least one memory that stores computer-executable components; and at least one processor that executes the computer-executable components stored in the at least one memory, wherein the computer-executable components comprise:

a signal processing component that receives signal data as the signal data is captured via an ultrasound transducer during a fetal monitoring session using doppler-based ultrasound technology;

a primary fetal heart rate (FHR) estimation component that determines, using a first process, first FHR values for a fetal heart targeted by the ultrasound transducer based on the signal data as the signal data is received;

a supervisory FHR estimation component that determines, using a second performed in parallel with the first process, second FHR values for the fetal heart based on the signal data as the signal data is received; and an error detection component that determines whether the first FHR values are associated with an error based on differences between the first FHR values and the second FHR values, wherein the error detection component identifies at least one of a double-count error, a half-count error, or a false value, and substitutes error-free second FHR values, and wherein the system further comprises a supervisory control component configured to regulate alarm generation or output rendering in response to error detection and to dynamically adjust averaging of at least one of the first and second FHR values based on computed signal-to-noise ratio values from segmented Doppler ultrasound signal data.

13. The FMS of claim 12, wherein the error comprises one or more of the FHR values corresponding to a false value.

14. The FMS of claim 12, wherein the error comprises at least one of, a double-count error or a half-count error.

15. The FMS of claim 12, wherein based on a determination that one or more of the first FHR values are associated with the error, the error detection component generates error information identifying the error, and wherein the computer-executable components further comprise:

a rendering component that renders the error information via an electronic output device in association with rendering FHR information indicating the first FHR values.

16. The FMS of claim 12, wherein the computer-executable components further comprise:

a rending component, wherein based on a determination that one or more of the first FHR values are associated with the error, the rendering component renders one or more of the second FHR values corresponding to the one or more first FHR values via an electronic output device as opposed to rendering the one or more of the first FHR values.

17. The FMS of claim 12, wherein the second process comprises:

dividing the signal data into consecutive signal data segments as a function of a windowed time interval as the signal data is received; and separately evaluating each segment of the consecutive signal data segments as they are generated in association with detecting signal peaks corresponding to heartbeats of the fetal heart, wherein the separately evaluating comprises, for each segment:

identifying one or more signal peaks included in the segment respectively corresponding to a heartbeat of the fetal heart; or determining that the segment excludes any signal peak corresponding to heartbeats.

* * * * *